(12) United States Patent
Albrecht et al.

(10) Patent No.: US 8,236,022 B2
(45) Date of Patent: Aug. 7, 2012

(54) IMPLANTABLE DEVICE FOR THE TREATMENT OF OBESITY

(75) Inventors: Thomas E. Albrecht, Cincinnati, OH (US); Mark S. Zeiner, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 377 days.

(21) Appl. No.: 12/147,984

(22) Filed: Jun. 27, 2008

(65) Prior Publication Data

US 2009/0326675 A1  Dec. 31, 2009

(51) Int. Cl.
*A61B 17/00* (2006.01)

(52) U.S. Cl. ........................................ 606/190

(58) Field of Classification Search ............ 128/897, 128/898; 606/151, 157; 623/23.65
See application file for complete search history.

(56) References Cited

U.S. PATENT DOCUMENTS

| | | | |
|---|---|---|---|
| 4,416,267 A | 11/1983 | Garren et al. | |
| 4,519,392 A | 5/1985 | Lingua | |
| 4,607,618 A | 8/1986 | Angelchik | |
| 4,925,446 A | 5/1990 | Garay et al. | |
| 5,129,915 A | 7/1992 | Cantenys | |
| 5,382,231 A | 1/1995 | Shlain | |
| 5,558,665 A | 9/1996 | Kieturakis | |
| 5,624,381 A | 4/1997 | Kieturakis | |
| 5,868,141 A | 2/1999 | Ellias | |
| 6,368,340 B2 | 4/2002 | Malecki et al. | |
| 6,558,400 B2 | 5/2003 | Deem et al. | |
| 6,656,194 B1 | 12/2003 | Gannoe et al. | |
| 6,705,989 B2 | 3/2004 | Cuschieri et al. | |
| 6,746,460 B2 | 6/2004 | Gannoe et al. | |
| 6,773,440 B2 | 8/2004 | Gannoe et al. | |
| 6,981,978 B2 | 1/2006 | Gannoe | |
| 6,994,715 B2 | 2/2006 | Gannoe et al. | |
| 7,033,373 B2 | 4/2006 | de la Torre et al. | |
| 7,033,384 B2 | 4/2006 | Gannoe et al. | |
| 7,044,957 B2 | 5/2006 | Foerster et al. | |
| 7,066,945 B2 * | 6/2006 | Hashiba et al. | 606/191 |
| 7,083,629 B2 | 8/2006 | Weller et al. | |
| 7,097,650 B2 | 8/2006 | Weller et al. | |
| 7,121,283 B2 | 10/2006 | Stack et al. | |
| 7,175,638 B2 | 2/2007 | Gannoe et al. | |
| 7,211,094 B2 | 5/2007 | Gannoe et al. | |
| 7,214,233 B2 | 5/2007 | Gannoe et al. | |

(Continued)

FOREIGN PATENT DOCUMENTS

EP  2103286 A1  9/2009

(Continued)

OTHER PUBLICATIONS

International Search Report dated Dec. 30, 2009; International Application No. PCT/US2009/048609.

*Primary Examiner* — Ryan Severson

(57) ABSTRACT

An implant for placement within a hollow body organ. The implant has a member with distal and proximal ends. The member has an undeployed shape for delivery to the hollow body and a deployed shape for implantation therein. The implant has at least one tensioning tether with a first end attached to at least one of the distal and proximal end and a second ends attached to the member between the distal and proximal ends. Wherein applying tension to the tether moves the member towards the deployed shape. The member preferably has a first rate at which it initially resists bending, and a second substantially higher rate at which it resists further bending.

8 Claims, 43 Drawing Sheets

U.S. PATENT DOCUMENTS

| | | |
|---|---|---|
| 7,220,237 B2 | 5/2007 | Gannoe et al. |
| 7,229,428 B2 | 6/2007 | Gannoe et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,503,922 B2 | 3/2009 | Deem et al. |
| 7,510,559 B2 | 3/2009 | Deem et al. |
| 7,708,684 B2 | 5/2010 | Demarais et al. |
| 7,753,870 B2 | 7/2010 | Demarais et al. |
| 7,753,928 B2 | 7/2010 | de la Torre et al. |
| 7,757,924 B2 | 7/2010 | Gerbi et al. |
| 7,789,848 B2 | 9/2010 | Gannoe et al. |
| 7,862,574 B2 | 1/2011 | Deem et al. |
| 7,909,838 B2 | 3/2011 | Deem et al. |
| 2004/0220682 A1 | 11/2004 | Levine et al. |
| 2005/0277975 A1 | 12/2005 | Saadat et al. |
| 2006/0106288 A1 | 5/2006 | Roth et al. |
| 2006/0155311 A1 | 7/2006 | Hashiba et al. |
| 2006/0217757 A1 | 9/2006 | Horndeski |
| 2007/0185518 A1 | 8/2007 | Hassier, Jr. |
| 2007/0239284 A1 | 10/2007 | Skerven et al. |
| 2007/0250020 A1 | 10/2007 | Kim et al. |
| 2007/0276428 A1 | 11/2007 | Haller et al. |
| 2008/0058840 A1 | 3/2008 | Albrecht et al. |

FOREIGN PATENT DOCUMENTS

| | | |
|---|---|---|
| WO | WO 2007/075978 A2 | 7/2007 |
| WO | 2008/028108 A2 | 3/2008 |

* cited by examiner

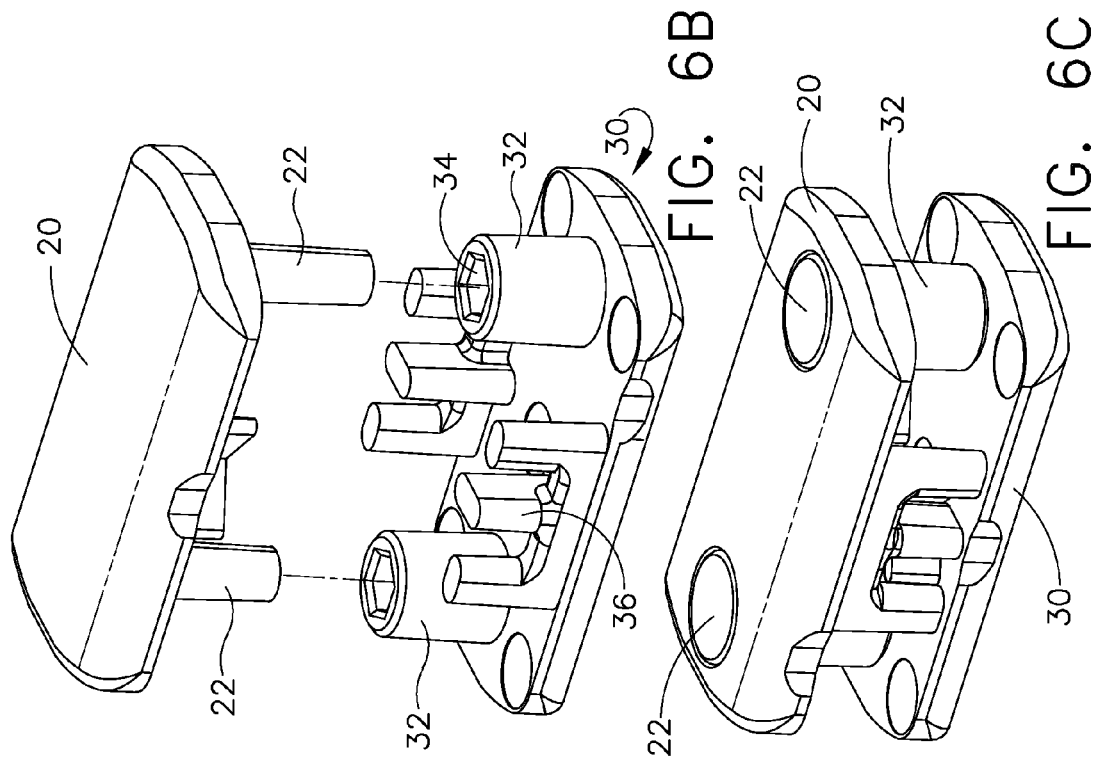
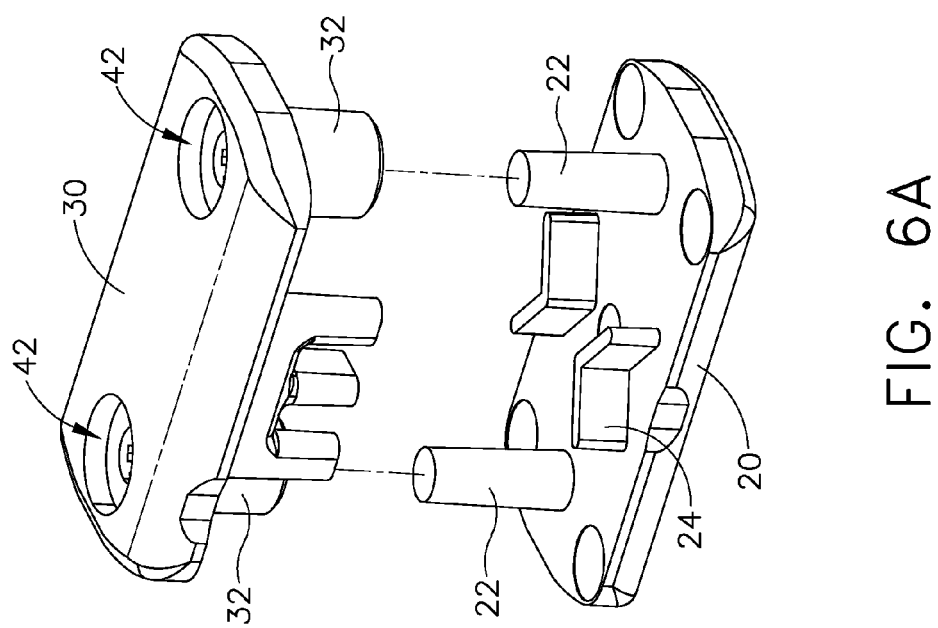
FIG. 6B
FIG. 6C
FIG. 6A

IMPLANTABLE DEVICE FOR THE TREATMENT OF OBESITY

FIELD OF THE INVENTION

The present invention relates generally to obesity treatment and, more particularly, to the treatment of obesity by implanting a force producing device into a gastric lumen to create pressure on the inside surface of the lumen to reduce the effective volume of the lumen and/or induce a sense of satiety in the patient.

BACKGROUND OF THE INVENTION

Obesity is a medical condition affecting more than 30% of the population in the United States. Obesity affects an individual's personal quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m2 and obesity as a BMI of 30 kg/m2. Morbid obesity is defined as BMI≧40 kg/m2 or being 100 lbs. overweight. Obesity and its co-morbidities are estimated to cost an excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure, a small stomach pouch is separated from the remainder of the gastric cavity and attached to a transected portion of the small intestine. This transected portion of the small intestine is connected between the "smaller" gastric pouch and a distal section of small intestine allowing the passage of food therebetween. The conventional RYGB procedure requires a great deal of operative time and is not without procedure related risks. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing an early feeling of satiety. A band is placed around the stomach near the junction of the stomach and esophagus. The small upper stomach pouch is filled quickly, and slowly empties through the narrow outlet to produce the feeling of satiety. In addition to surgical complications, patients undergoing a gastric banding procedure may suffer from esophageal injury, spleen injury, band slippage, reservoir deflation/leak, and persistent vomiting. Other forms of bariatric surgery that have been developed to treat obesity include bilio-pancreatic diversion, vertical banded gastroplasty and sleeve gastrectomy. As aspects of some of these procedures, including RYGB, involve stapling a portion of the stomach, many bariatric procedures are commonly referred to as "stomach stapling" procedures.

For morbidly obese individuals, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss. Further, it is known that modest reductions in weight may significantly decrease the impact of co-morbid conditions including, but not limited to type 2 diabetes mellitus. For this reason as well, a low cost, low risk procedure with effective weight loss results would provide significant benefit to both patients and health care providers.

Accordingly, it is desirable to have a low risk, minimally invasive procedure for treating obesity. It is desirable to have a procedure in which a treatment device can be easily and safely implanted into the gastric cavity of a patient to reduce the effective volume of the cavity. Additionally, it is desirable to have such a device that can assume an initial deploying configuration, and then be transformed into a second operable configuration within the gastric cavity. Further, it is desirable that the device apply outward pressure against the wall of the gastric cavity in the operable configuration in order to create a sensation of fullness within the patient. Further, it is desirable to have a method of treating obesity by reducing the effective volume within the gastric cavity. Additionally, it is desirable to have a method of treating obesity which includes applying pressure against the inside surface of the gastric cavity to create a feeling of fullness. It is desirable that the obesity treatment method be low cost and minimally invasive so as to be beneficial to a large number of obese patients. Further, it is desirable that the obesity treatment be easily and safely reversible. The present invention provides an implantable obesity treatment device and method of treating obesity which achieves these objectives.

SUMMARY OF THE INVENTION

The present invention provides an implantable device for placement within a hollow body organ having an undeployed shape for delivery to the hollow body organ and a deployed shape within the hollow body organ. The device includes tensioning members for drawing and locking the ends of the device in a curved, deployed shape. Retained forces within the deployed device produce outward pressure on the hollow body organ to flatten the organ in the plane of the device, thereby reducing the effective volume within the organ.

The present invention also provides a method for treating obesity which includes passing an implantable device into a hollow body organ in an undeployed configuration and placing the device into a deployed configuration within the hollow body organ. The method includes drawing and holding the ends of the device in a curved configuration. In the curved configuration, pressure is applied by the device against the interior of the hollow body organ, to flatten the organ in the plane of the device, thereby reducing the volume within the organ.

BRIEF DESCRIPTION OF THE DRAWINGS

FIG. 6A is an isometric view of the components aligned for attachment, showing in detail the inner surface of the male component;

FIG. 6B is an isometric view similar to FIG. 6A, showing the components aligned for attachment, with the position of the components reversed to show the inner surface of the female component;

FIG. 6C is an isometric view showing the components attached together to form a segment;

DETAILED DESCRIPTION OF THE INVENTION

Figure 1:
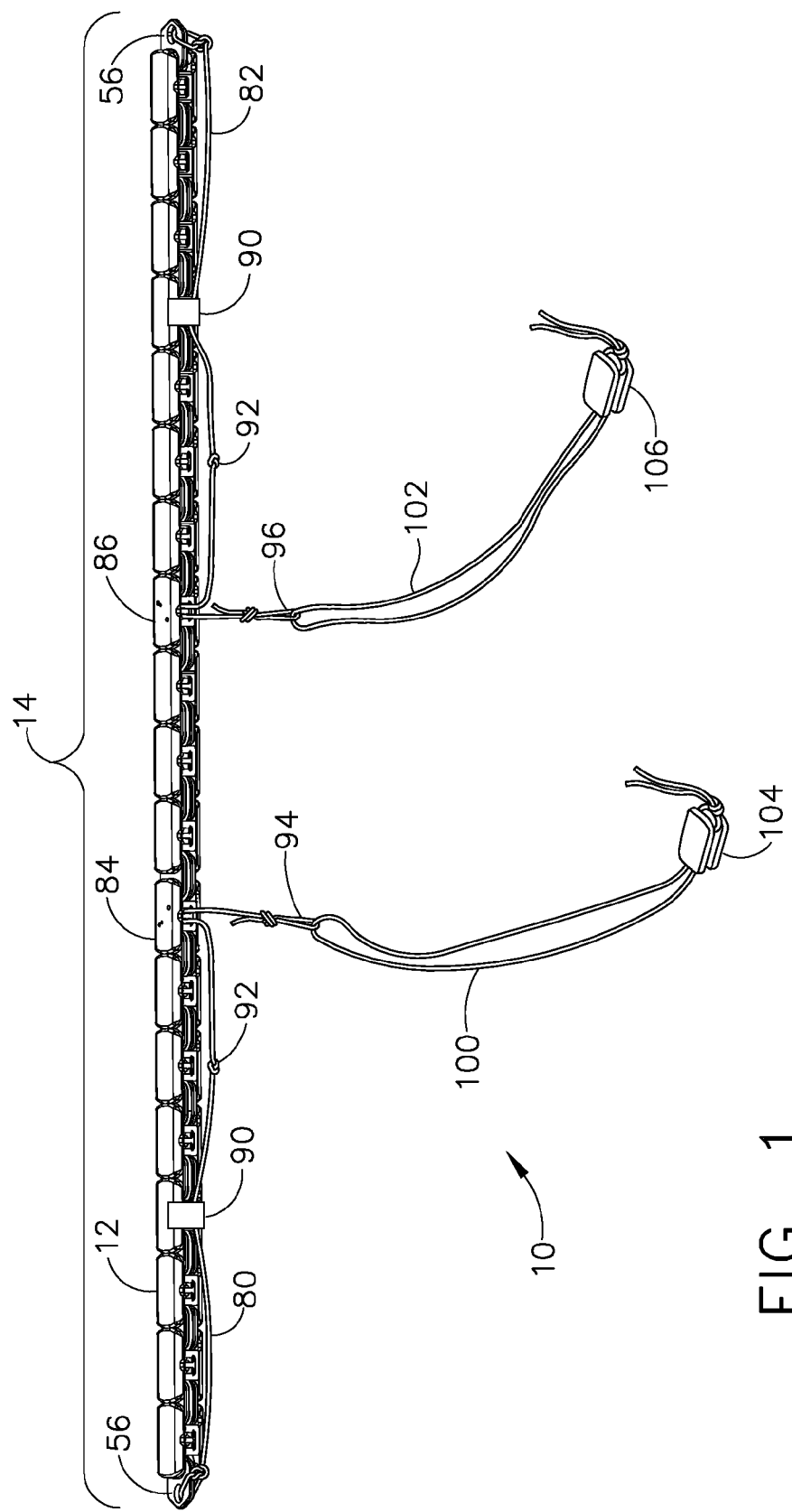
FIG. 1 is an overall view of a first embodiment of an implantable obesity treatment device of the present invention.

Referring now to the drawing figures, in which like numerals indicate like elements throughout the views, FIG. 1 illustrates a first exemplary obesity treatment device 10 of the present invention. The obesity treatment device is designed to be implanted in the gastric cavity to hold the gastric wall largely taut, reducing the effective volume per tissue surface area within the cavity. The pressure of the device on the gastric wall biases stretch receptors in the gastric cavity to induce a prolonged hormonal response within the body that reduces the patient's appetite and desire to eat. The device can be delivered into the gastric cavity in an undeployed, substantially linear shape and then manipulated into a substantially curved, deployed shape within the cavity. Inside the gastric cavity, the deployed device applies an outward radial force in a single plane flattening the cavity. The plane in which the device resides may change over time due to stomach motions. The preferred device can be easily installed and removed endoscopically. Although less desirable, laparoscopic, open surgical techniques, or a combination of surgical methods, may also be used to implant the device.

As shown in FIG. 1, device 10 comprises a plurality of individual, oblong segments 12 connected end-to-end to form a flexible implant member 14. Member 14 can have an exterior surface with an elastomeric coating When connected, each of the segments 12 can be flexed relative to the other segments in a common plane. The segments are sized to allow for transesophageal passage through an overtube into the gastric lumen, and are composed of a biocompatible material that is not absorbed or degraded over time by the acids and other enzymes present in the gastric lumen. Suitable materials for use in the implant device include, for example, High Density Polyethylene HDPE injection molded plastic, Polyetheretherketone (PEEK), Polypropylene (PP), Low Density Polyethylene (LDPE), and Polysulfone (PSU). These materials are representative of the biocompatible materials suitable for use in device 10. Other biocompatible materials known to those skilled in the art may also be used within the implant device of the present invention without departing from the scope of the invention. A radio-opaque additive, such as barium sulfate, may be combined with the biocompatible material to enhance visualization of the device. Different color additives can be blended into the material of different segments for distinguishing between the segments while under direct or endoscopic visualization. The color variations can be used to differentiate between proximal, center and distal sections of implant member 14. As an alternative to different color additives, the individual segments may be numbered in order to distinguish between the sections of the implant member.

Figure 2:
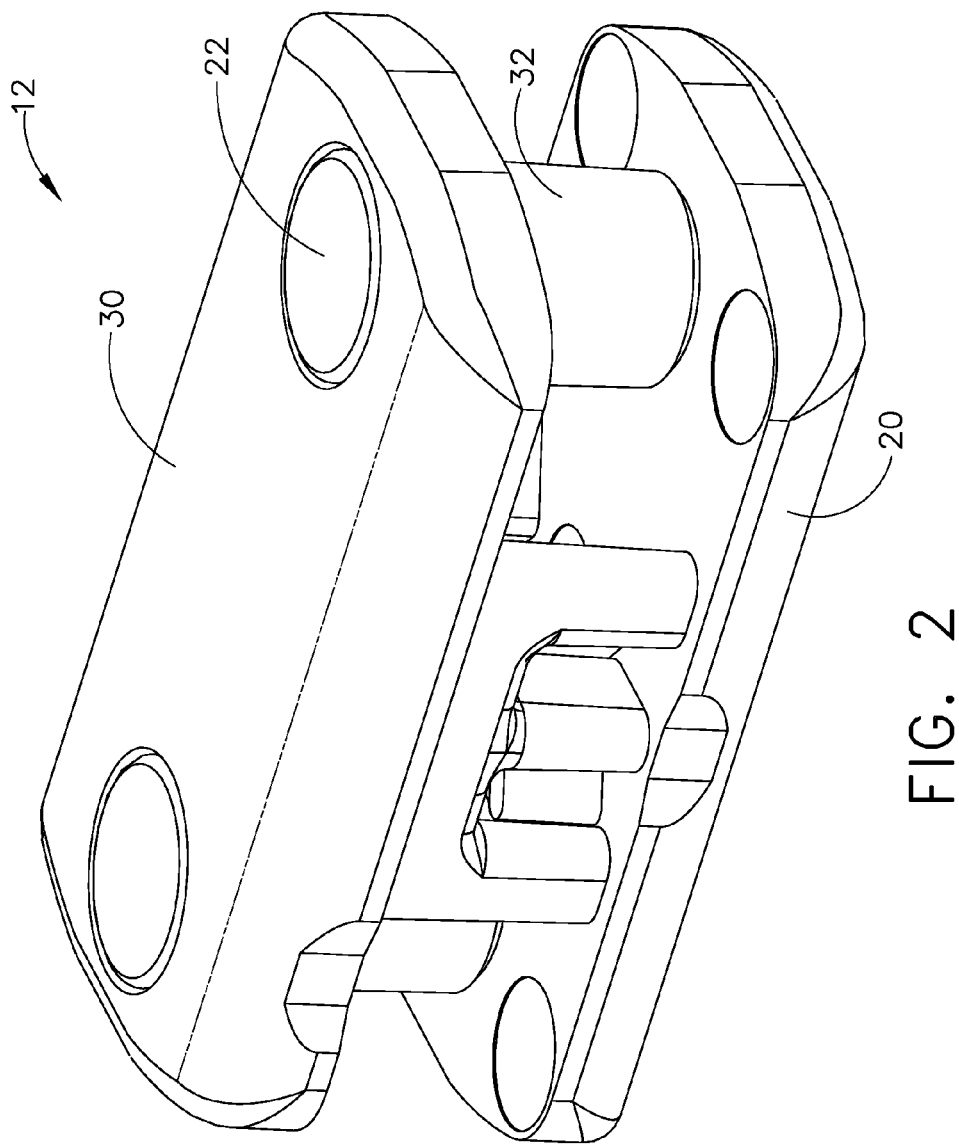
FIG. 2 is an isometric view of a single segment of the implant device.
Figure 3:
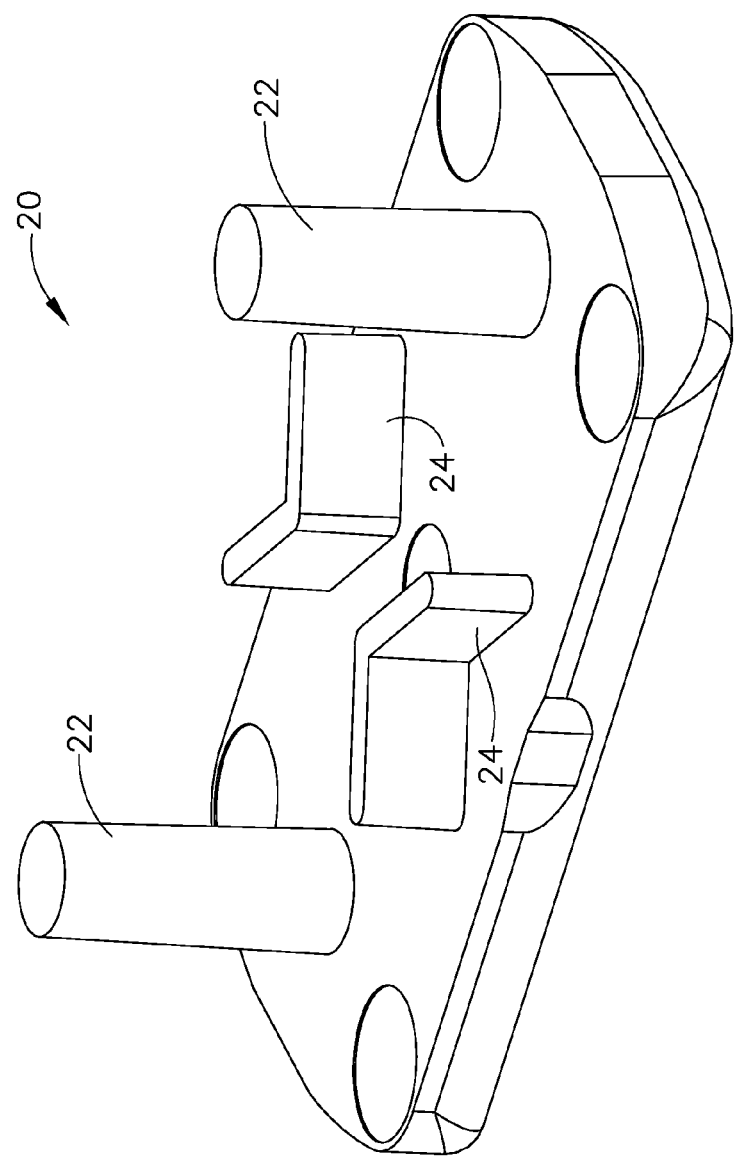
FIG. 3 is an isometric view of the male component of the segment shown in FIG. 2.
Figure 4:
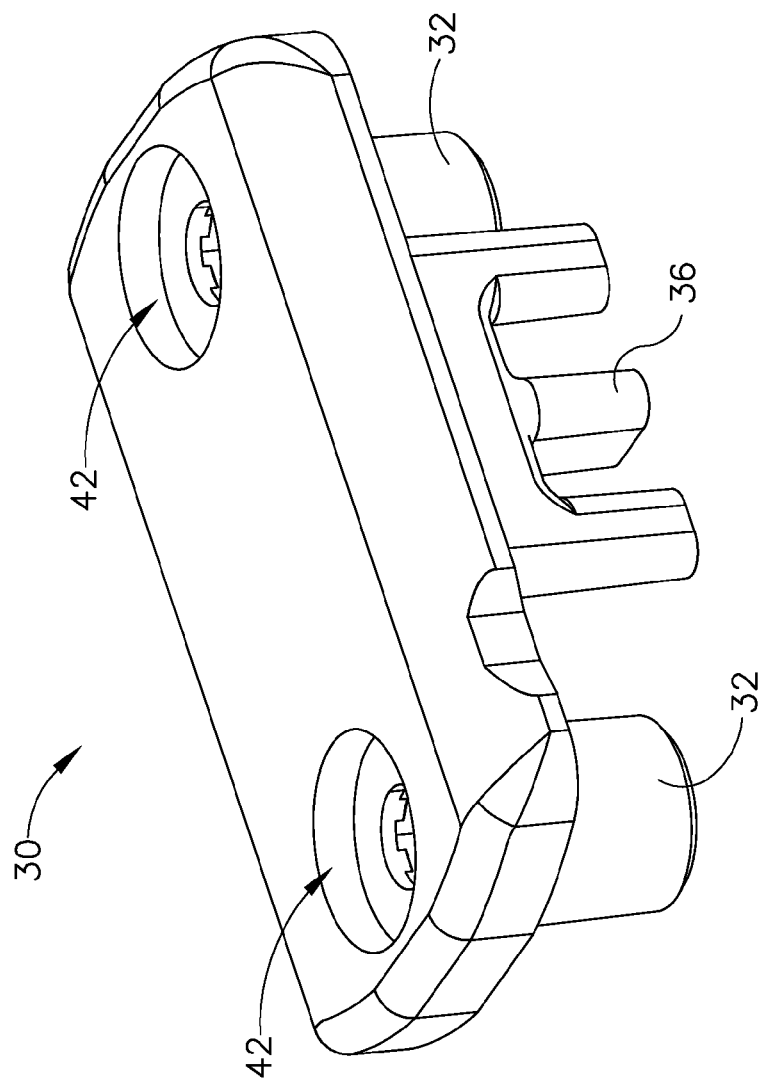
FIG. 4 is an isometric view of the female component of the segment shown in FIG. 2, showing the counter bore.
Figure 5:
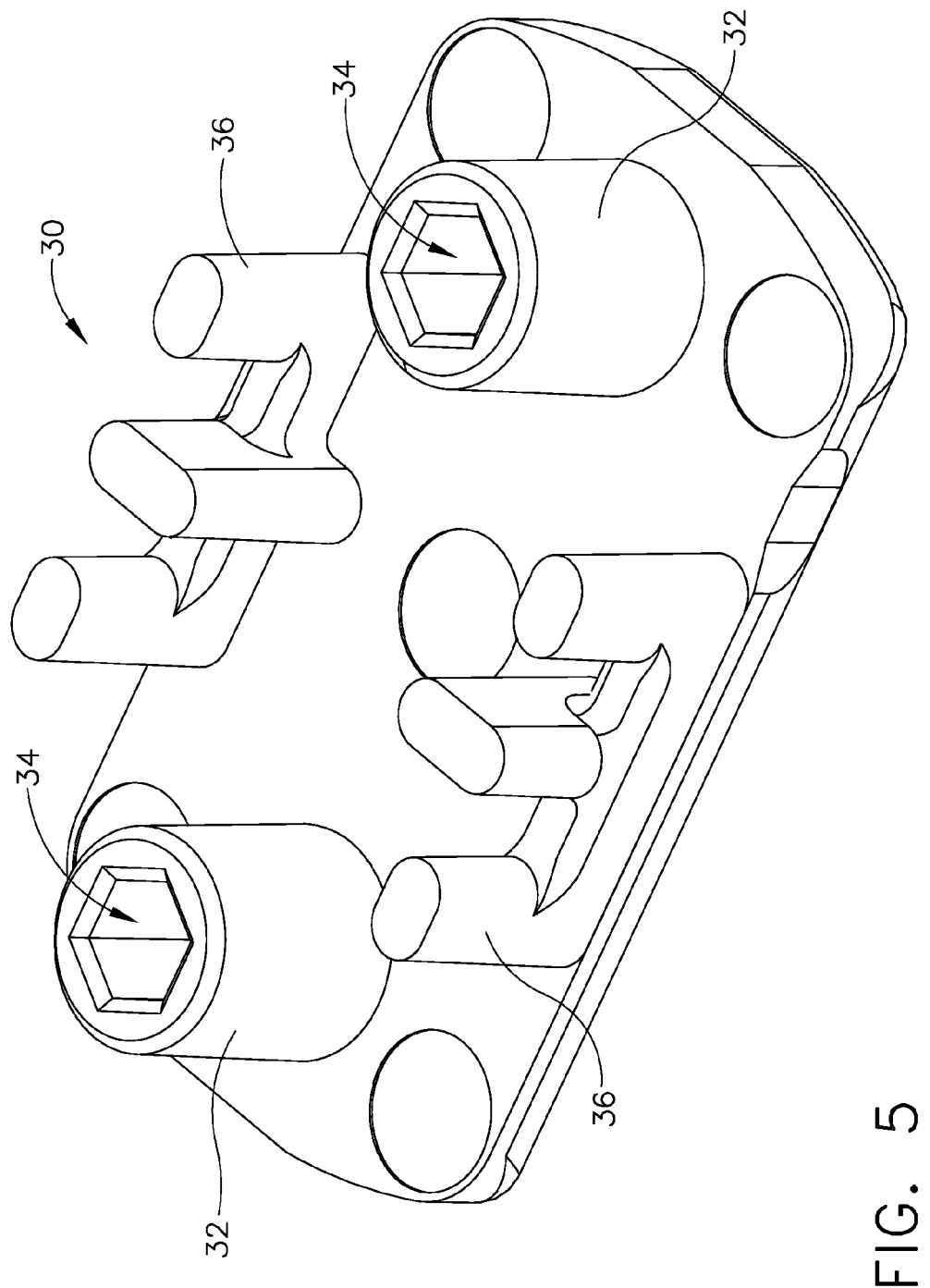
FIG. 5 is an isometric view showing the pivot bosses of the female component.

FIG. 2 shows an individual segment 12 comprising a pair of mating components secured together along the longitudinal midsection of the segment. The male component 20, shown independently in FIG. 3, includes pins 22 extending perpendicularly from the inner face of the component. In the preferred embodiment shown, male component 20 includes a pair of pins 22 that are symmetrically positioned adjacent opposing ends of the component. Pins 22 have a cylindrical shape with a slight inward taper in a direction away from the inner component face. Between pins 22, pairs of ribs 24 project outward along the longitudinal sides of the component. FIGS. 4 and 5 illustrate an exemplary female component 30 having a pair of pivot bosses 32 with bores 34 formed therethrough. Pivot bosses 32 project perpendicularly from the inner surface of component 30. Pivot bosses 32 are symmetrically positioned adjacent opposing ends of component 30 so as to be vertically aligned with pins 22 when the components are mated together, as shown in FIGS. 6A-6C. Brackets 36 are located along the longitudinal sides of female component 30. Brackets 36 comprise a plurality of spaced posts. Ribs 24 extend on the inside of the bracket posts when components 20, 30 are joined together to form a segment 12.

Figure 7:
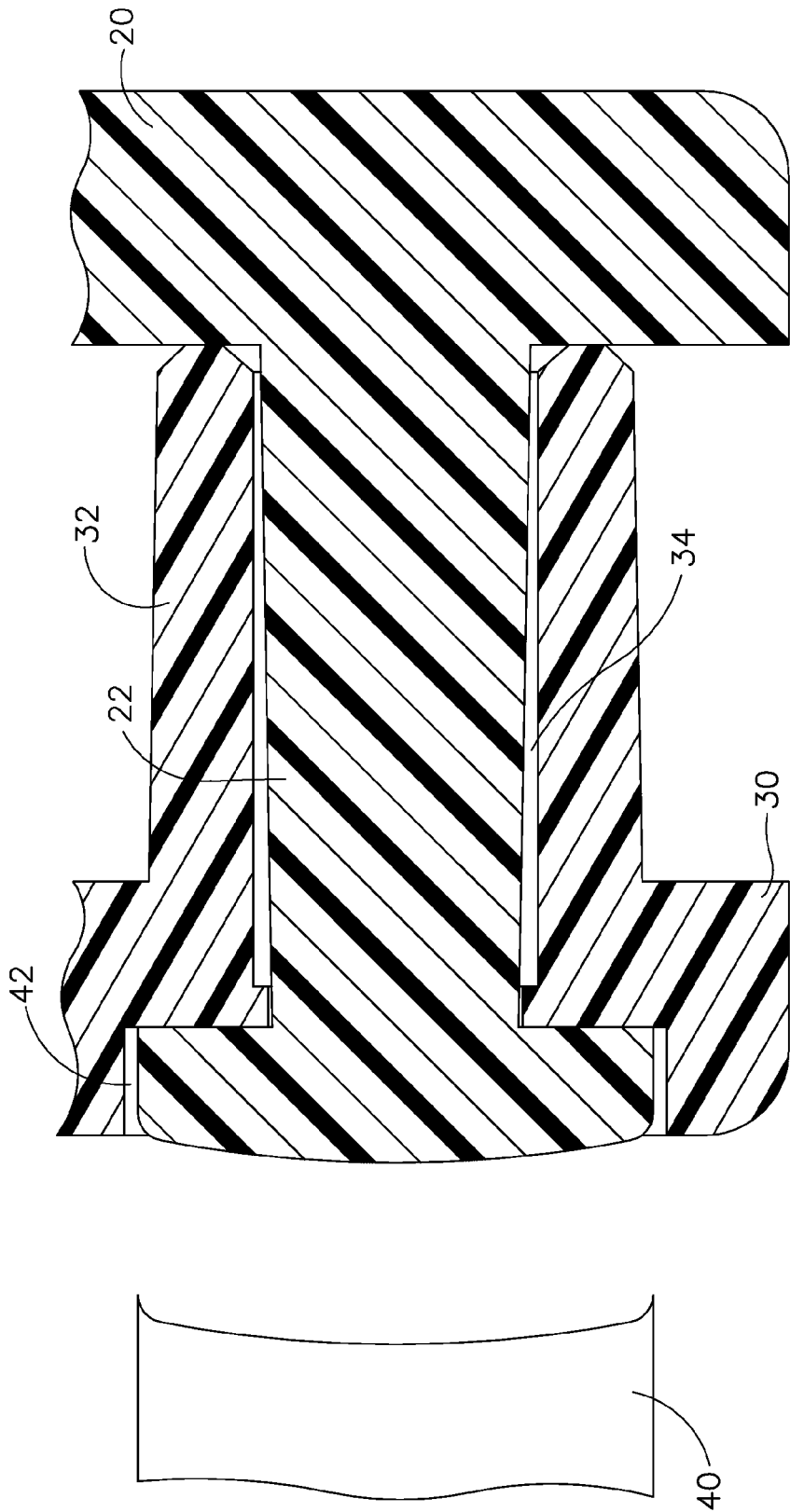
FIG. 7 depicts a heat stake tool aligned with a pin for securing the segment components together.

In the exemplary embodiment shown, segment components 20, 30 are securely attached by inserting pins 22 through bores 34. The inward taper of pins 22 facilitates insertion into bores 34. Preferably, bores 34 have a non-cylindrical shape, such as the hexagonal shape shown in FIG. 5, so that the cylindrical pins 22 are press fit into the bores to form a more secure attachment between the pin and bore. Pivot bosses 32 are shorter than pins 22 to allow the pins to be inserted fully through bores 34. To further secure components 20, 30 together, a heat stake forming tool may be applied to the tip of each pin 22, after insertion into bore 34, to expand the diameter of the pin end. FIG. 7 shows a representative heat stake forming tool 40 being applied to the tip of a pin 22 after the pin has been inserted into bore 34. A counter bore 42 can be formed in the outer surface of female component 30 to provide for contact between heat stake tool 40 and pin 22. As the tip of pin 22 is heated by tool 40, the pin material softens and expands, filling bore 42, as shown in FIGS. 2 and 7. The increased tip diameter of pin 22 prevents the pin from pulling out of the pivot boss 32.

FIGS. 6A-6C show the alignment between pins 22 and bosses 32 during assembly of a segment 12. Pins 22 are vertically aligned with bores 34 in pivot bosses 32, while ribs 24 are aligned with brackets 36. Placing pins 22 within bores 34, and ribs 24 between brackets 36, securely attaches components 20, 30 together to form a segment 12. In addition to the pin/bore connection method described above, numerous other types of fastening features known to those skilled in the art may be utilized for assembling segments 12. Other types of fastening features include screws, rivets, and snaps, among others, which may be incorporated into components 20, 30 and used during assembly to affix the components.

Figure 8A:
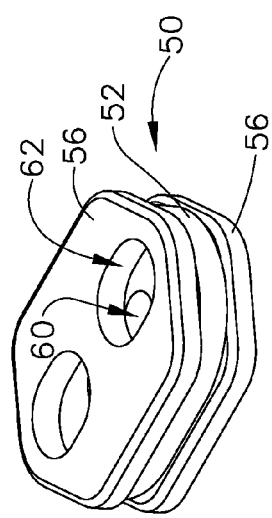
FIG. 8A is an isometric view of the link assembly.
Figure 8B:
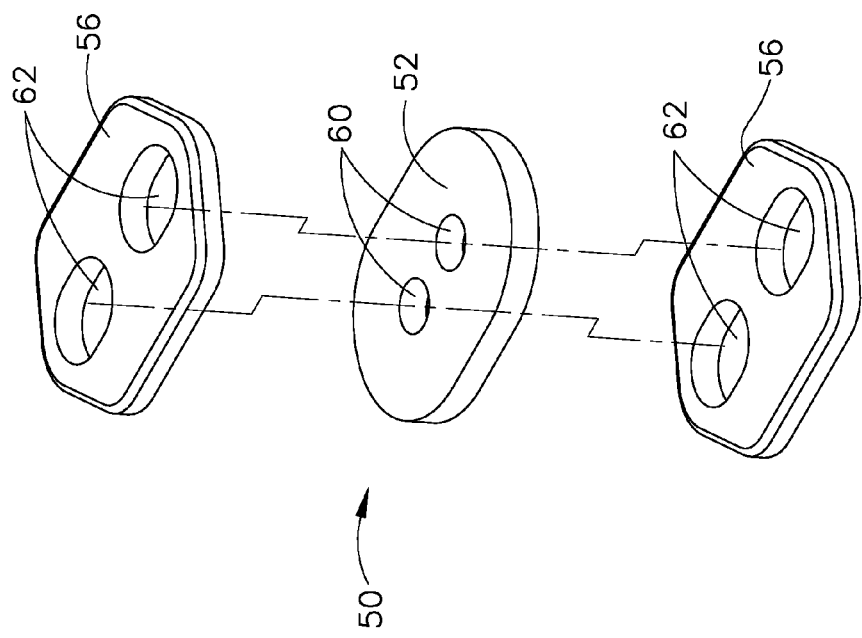
FIG. 8B is an exploded view of the link assembly of FIG. 8A.
Figure 9:
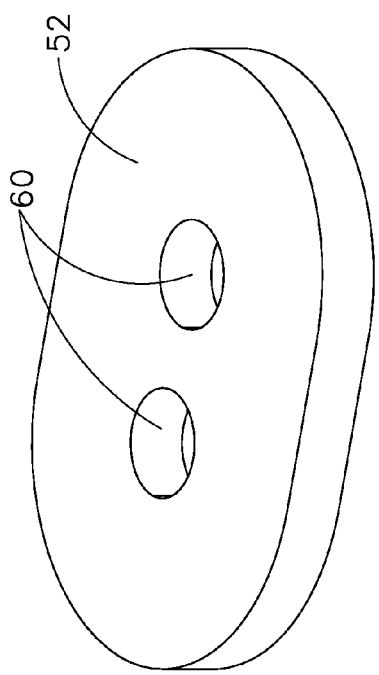
FIG. 9 is an isometric view of the link assembly disk.

To form implant member 14, adjoining segments 12 are connected together in an end to end relationship by a linking assembly. The linking assembly holds the segments together, while allowing a range of relative movement between adjoining segments. As shown in FIG. 8A, a representative linking assembly 50 comprises a deformable, semi-rigid disk 52 stacked between a pair of rigid links 56. Disk 52 is comprised of an elastic material that enables the disk to stretch and deform in response to pressures as the adjoining segments 12 are moved relative to each other. As shown in FIG. 9, disk 52 includes a pair of circular openings 60 between the upper and lower disk surfaces. Openings 60 are longitudinally spaced apart and symmetrically positioned in the center of disk 52. The diameter of openings 60 is smaller than the diameter of pivot bosses 32. Openings 60 are stretched during assembly over pivot bosses 32 to form a tight fit between the openings and bosses. Links 56 have a hexagonal shape with pairs of inwardly angled edges at the distal and proximal ends. A pair of openings 62 is spaced along the longitudinal axis of each link 56. Openings 62 have an oval shape, with the longer sides of the openings extending in the longitudinal direction of the link. When links 56 and disk 52 are stacked, as shown in FIG. 8B, openings 62 are vertically aligned with holes 60 to allow linking assembly 50 to be mounted on pivot bosses 32.

Figure 11:
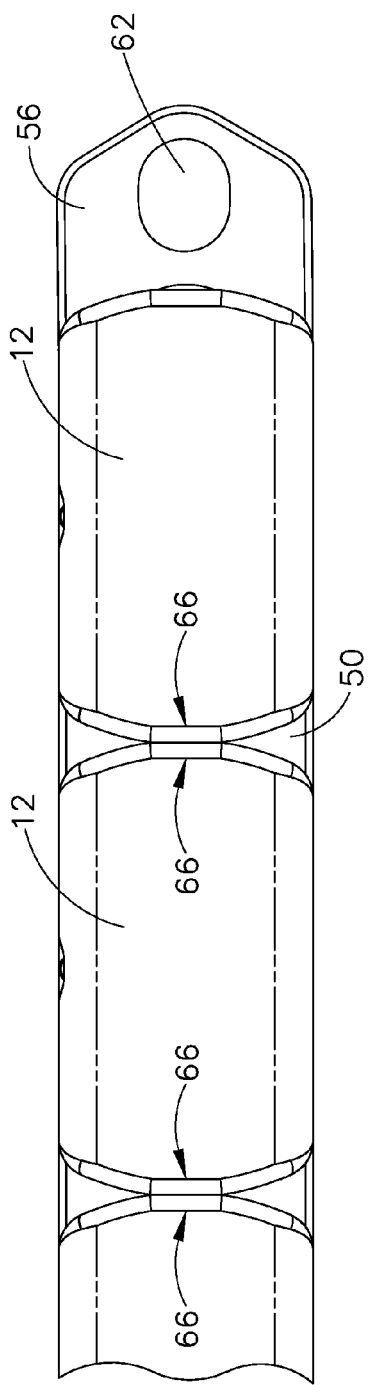
FIG. 11 is a top view of an end of the implant member showing the member segments in a straight configuration.
Figure 10:
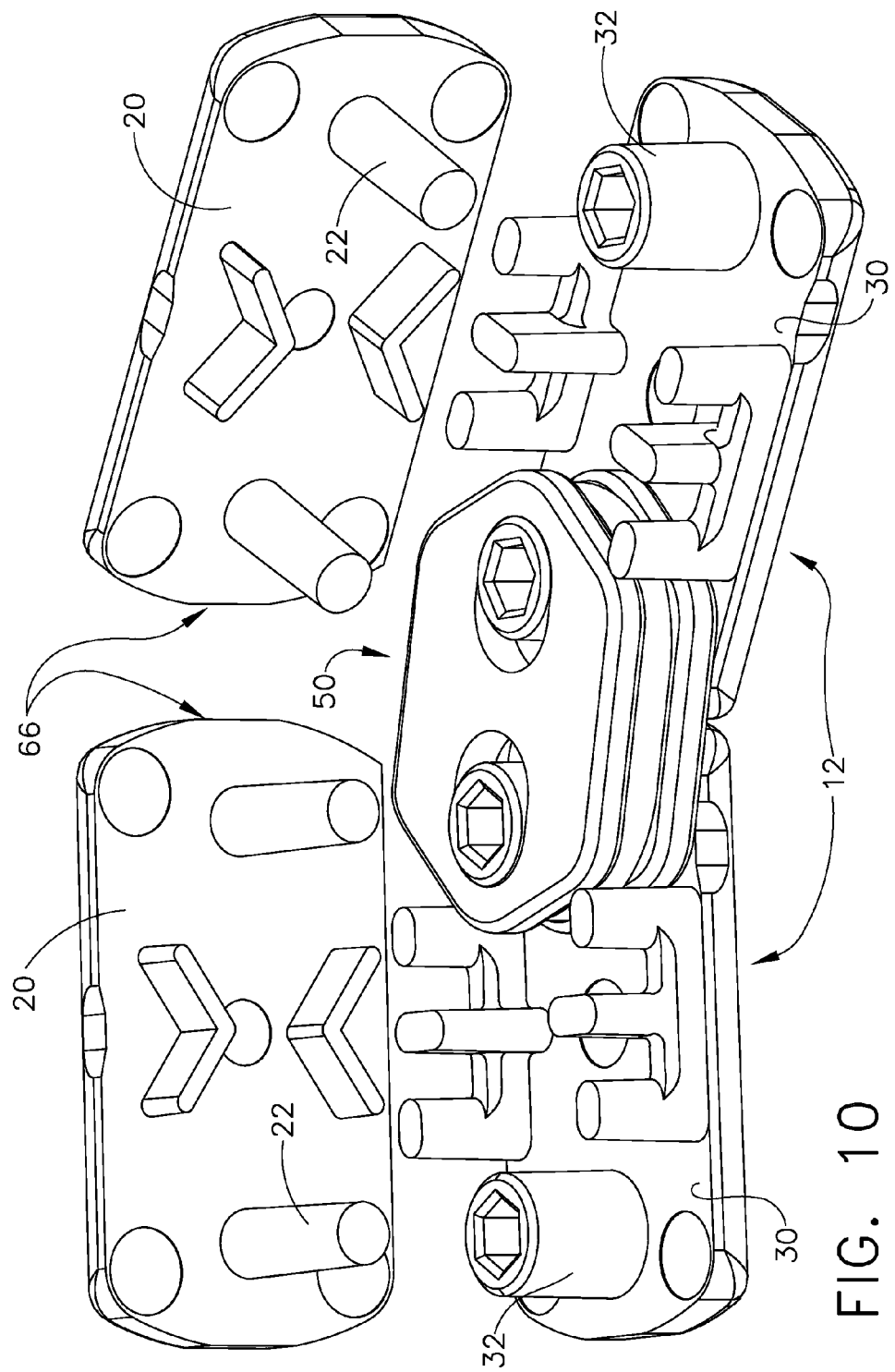
FIG. 10 is an isometric view showing the link assembly and adjoining segments in a bent configuration, with the male components pulled back to show the link assembly mounted on the pivot bosses.
Figure 12:
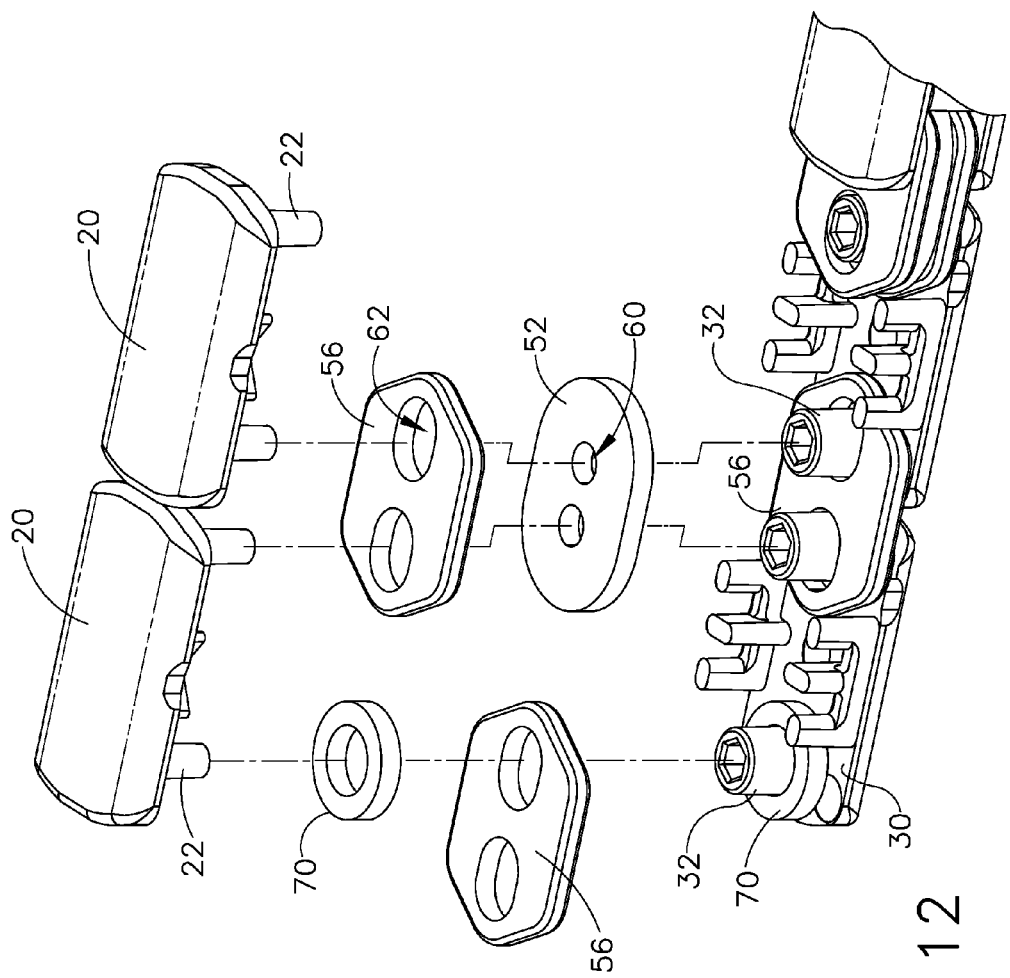
FIG. 12 is an exploded view of the proximal end of the implant member.

Implant member 14 is assembled by placing a linking assembly 50 between each adjoining pair of segments 12, so that the segments and linking assemblies alternate along the length of the member. When assembled, the height of linking assembly 50 is slightly less than the gap between the assembled components 20, 30 to allow some out of plane flexibility between the linking assembly and segments. FIG. 10 shows a linking assembly 50 located between a pair of segments 12, with pivot bosses 32 extending through openings 60, 62. A pivot boss 32 from the distal segment passes through one set of the openings 60, 62, while a second pivot boss from the immediate proximal segment extends through the second set of the linking assembly openings. Disk 52 is stretched between and over the pivot bosses 32 to mount the disk on the bosses. When assembled, the elastic quality of disk 52 draws the pivot bosses and, thus, the adjoining segments 12 together in a straight end-to-end configuration, as shown in FIG. 11. Segments 12 include flat sections 66 centered along the adjoining ends. Flat sections 66 abut when disk 52 pulls the adjoining segments 12 together. Drawing the flat surfaces on the adjoining segment ends together produces a self-straightening effect on the implant member. In the straight, undeployed shape, the distance between disk openings 60 is at a minimum, and pins 22 are positioned in the inner arc of link openings 62, as shown in FIG. 12. Linking assemblies 50 provide a gap filling feature between adjoining segments 12, as shown in the flexed configuration in FIG. 10 and the straight configuration in FIG. 11. By filling gaps along the sides of the adjoining segment ends, linking assemblies 50 prevent tissue from getting caught or pinched between the segments.

Figure 13:
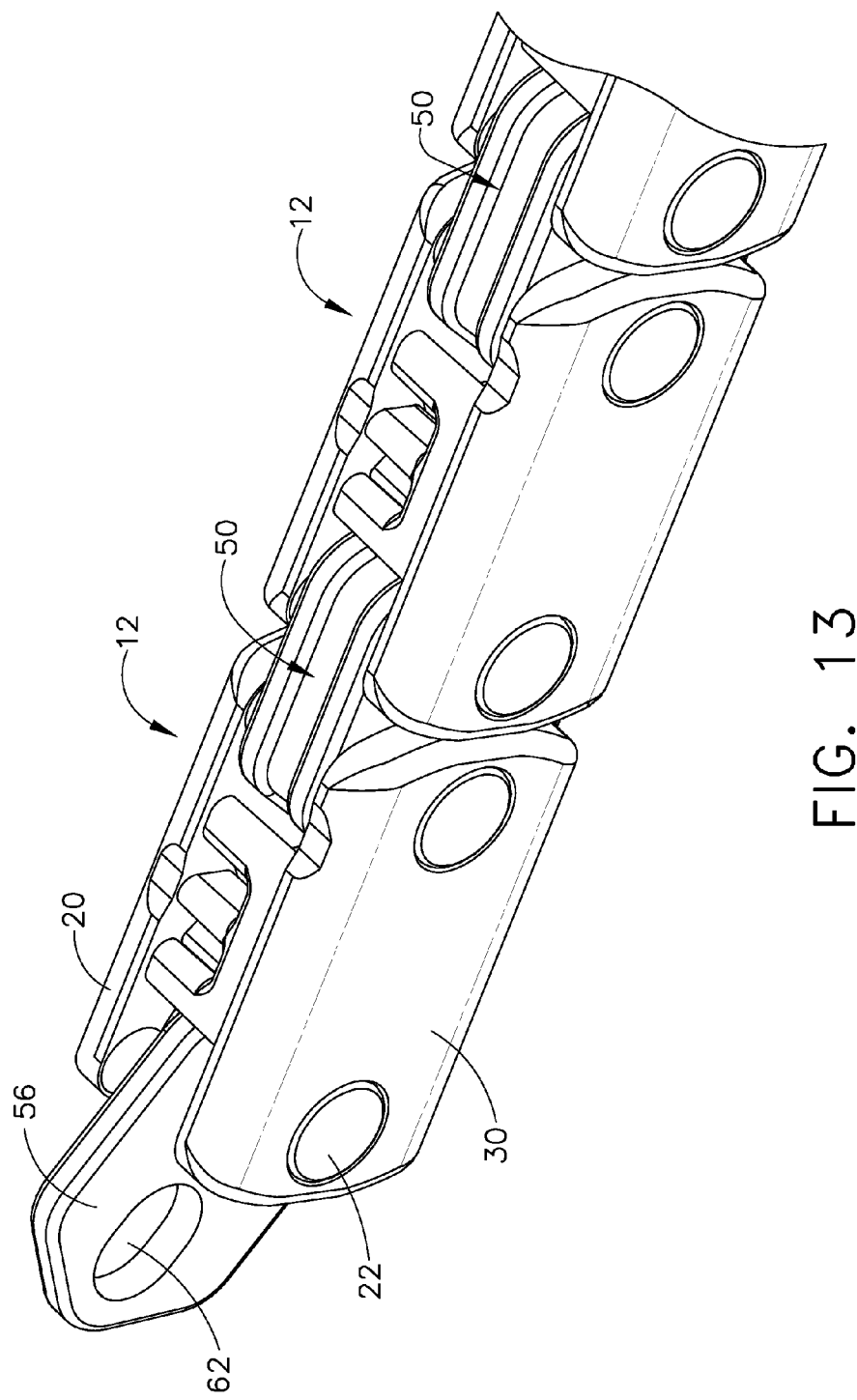
FIG. 13 is an isometric, close up view of the distal end of the implant member.

At the ends of implant member 14, a single link 56 is mounted over the distal most and proximal most pivot bosses 32. As shown in FIG. 13, the link 56 is mounted with a link opening 62 extending out from the end of the member. One or more spacers 70, shown in FIG. 12, may be mounted on pivot bosses 32 above and/or below the end links 56 to allow the links to flex relative to the end segment. Spacers 70 can be comprised of any biocompatible material, however, using a biocompatible material such as, for example, stainless steel, which can be visualized through fluoroscopy, enables the spacers to also be used as end identifiers during device deployment. In additional to material composition, the shape and number of spacers may also be varied at the proximal and distal implant member ends to distinguish between the ends with fluoroscopy. For example, placing two stainless steel spacers on the distal end of the implant member, and one stainless spacer and one plastic spacer on the proximal end of the member, enables the ends to be distinguished because two spacers are visible on the distal end while only one spacer is visible on the proximal end. Likewise, the outer circumferential shape of the spacers can be varied between the proximal and distal ends, such as, for example, from a circular shape to a scalloped, square or other distinguishable shape. The shape differences can be detected with the fluoroscope in order to distinguish between the implant member ends during deployment.

Figure 14:
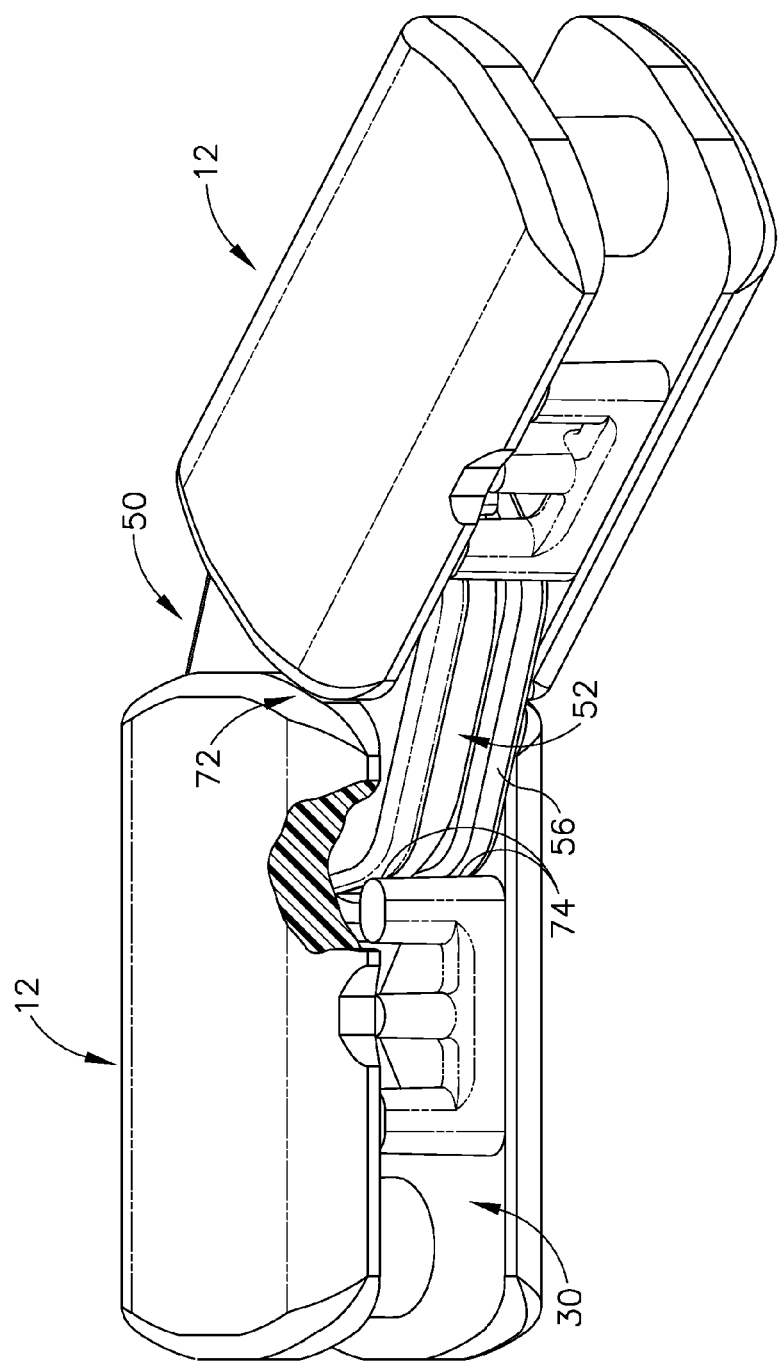
FIG. 14 is an isometric view showing a link assembly and adjoining segments in a bent configuration.

Linking assembly 50 provides for limited flexing between adjacent segments 12, enabling implant member 14 to bend during delivery and implantation. The degree of flexing between segments 12 is controlled in part by the size of link openings 62. As segments 12 pivot relative to linking assemblies 50, the position of pivot bosses 32 within openings 62 varies. When segments 12 are configured in a straight line, pivot bosses 32 are located at the inside arc of openings 62, as shown in FIG. 12. As the segments pivot relative to an attached linking assembly 50, the position of pivot bosses 32 shifts from the inside arc towards the outside arc of link openings 62. As segments 12 flex relative to linking assembly 50, deformable disks 52 provide increased resistance to bending the more segments 12 are flexed, due to the stretching of the disk between the pivot bosses. Once pivot bosses 32 bottom out against the outer arc of link openings 62, as shown in FIG. 10, the pivot bosses produce substantial resistance to further intersegment bending Resistance to further bending between adjacent segments 12 is also provided by contact between the outer corners of the segments, as indicated by reference numeral 72 in FIG. 14. As segments 12 flex, the segments move from contact between flat ends 66 to contact between the outer corners. Contact between the outer corners 72 can occur on both sides of flat ends 66 to limit flexing of segments 12 in either direction relative to the longitudinal link axis. The abutting corner edges 72 prevent further relative rotation of the segments. Additionally, as segments 12 flex relative to linking assembly 50, brackets 36 within the segments rotate into contact with the linking assembly. Brackets 36 contact links 56 at an outside corner between the inwardly angled edges and longitudinal side, as indicated at reference numeral 74 in FIG. 14. The contact between brackets 36 and links 56 provides an additional positive stop preventing over flexing of segments 12.

The bending angle between segments 12 is controlled to maintain a minimum diameter within the deployed implant device. When fully deployed, the distal and proximal ends of implant member 14 are flexed into a curvilinear shape extending towards the interior of the lumen. A minimum diameter is maintained in the deployed device ends to prohibit migration of the device out of the gastric cavity and into adjoining lumens, such as through the pylorus into the intestinal lumen. The maximum bending angle between segments is determined by the degree of bending that will result in the device ends being curved into the minimum desired diameter. Locking the distal and proximal implant member ends at a predetermined bending angle also increases the stiffness of the device, enabling the device to exert an outward pressure on the wall of the gastric cavity. This outward pressure on the cavity wall flattens the cavity within the plane of the device. The outward pressure also stretches the cavity wall, thereby causing receptors within the cavity to send a signal of fullness or satiety to the brain of the patient. The satiety signal produces a feeling of fullness in which the patient lacks the desire or appetite for further food consumption. The implant member can also elute a medicine that would produce a satiety signal or other therapeutic or treatment effect.

Figure 15:
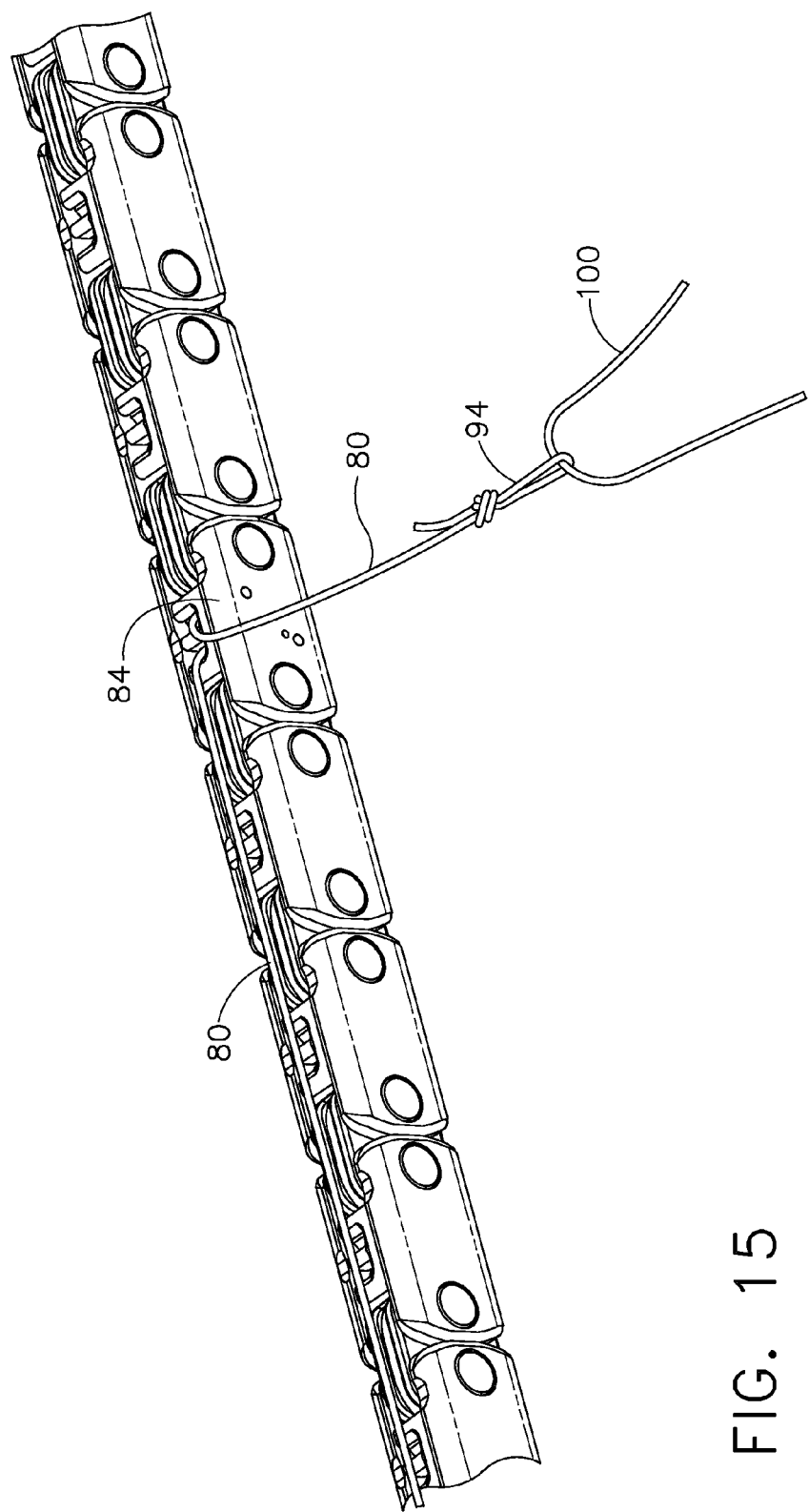
FIG. 15 is an isometric view of the distal string lock, showing the tensioning string and pull cable.
Figure 16:
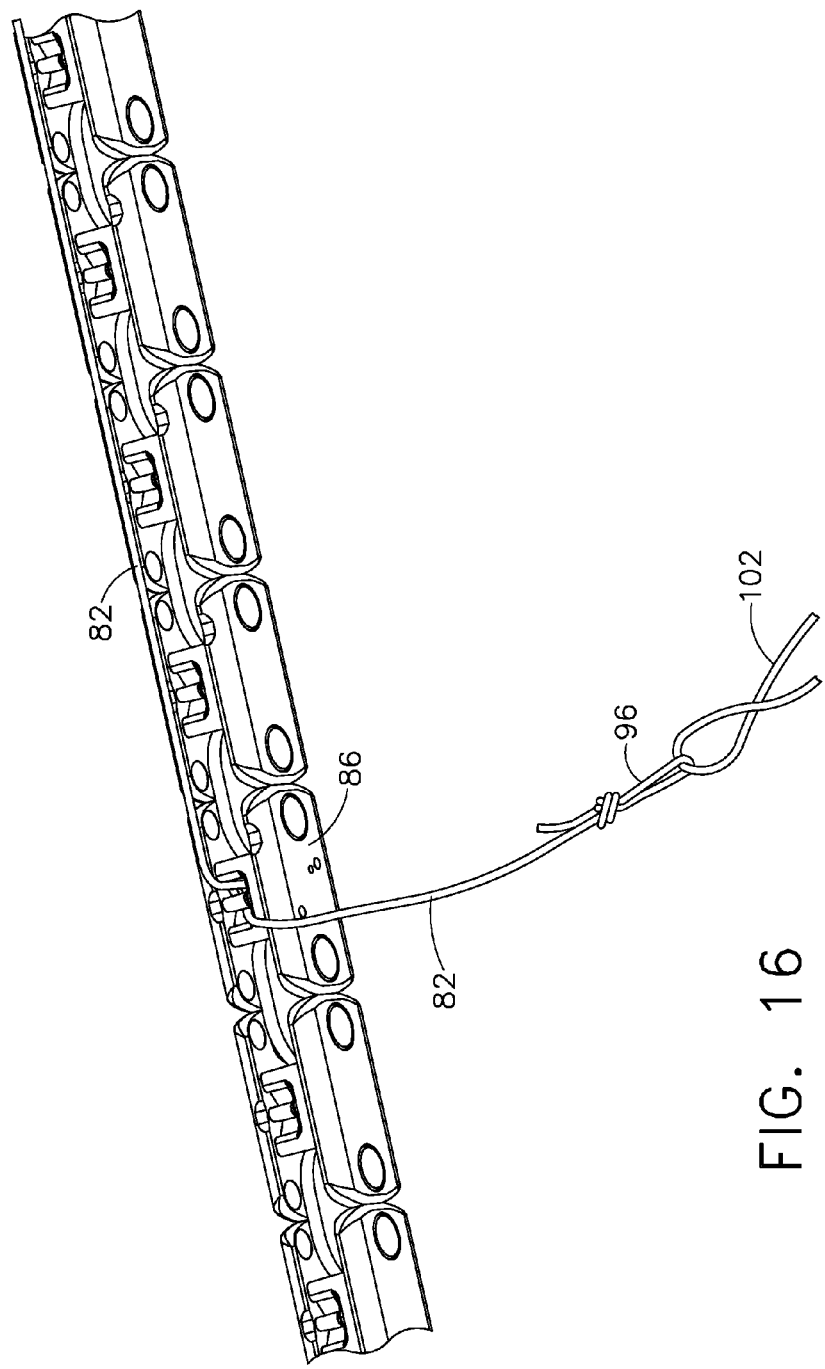
FIG. 16 is an isometric view of the proximal string lock, showing the tensioning string and pull cable.

Device 10 comprises a deployment mechanism for bending the implant member into a substantially open planar implantation shape. The deployment mechanism includes tensioning members for curving the distal and proximal member ends during implantation. The tensioning members preferably comprise one or more elongated pieces of a flexible material such as, for example, cable, string, wire, suture, or any other similar, suitable, biocompatible material which serve as a tether between points on the implant member. In the embodiment shown in FIG. 1, the tensioning members comprise strands of string with a first string 80 attached to the distal end link 56, and a second string 82 connected to the proximal end link 56. Tensioning strings 80, 82 extend from end links 56 to separate locking segments 84, 86 located along the length of implant member 14. Between end links 56 and locking segments 84, 86, tensioning strings 80, 82 are preferably releasably retained against member 14. Strings 80, 82 can be retained against member 14 by tapes 90, such as shown in FIG. 1, or by any other suitable retaining means known in the art. A locking feature is located on each of the tensioning strings 80, 82 between end links 56 and locking segments 84, 86. The locking feature can be a knot 92, as shown in the Figures, or any other size enhancing element. Knots 92 are located at predetermined positions along the length of tensioning strings 80, 82. The positions of knots 92 are dependent upon the desired deployed diameter of the member ends. From locking segments 84, 86, tensioning strings 80, 82 extend outward to form loops 94, 96 at the end of the strings. Removable pull cables are attached to each tensioning string through loops 94, 96; with a distal pull cable 100 passing through the distal string loop 94, as shown in FIG. 15, and a proximal pull cable 102 passing through the proximal string loop 96, as shown in FIG. 16. The ends of pull cables 100, 102 are connected to separate pull blocks 104, 106 associated with the distal and proximal ends respectively, as shown in FIG. 1.

As mentioned above, locking segments 84, 86 are located along the length of implant member 14. Tensioning strings 80, 82 extend from the distal and proximal end links 56 through the locking segments. In the embodiment shown, the first locking segment 84 is located between the distal end and midpoint of the device 10, while the second locking segment 86 is located between the proximal end and midpoint of the device. The location of the locking segments along the length of implant member 14 depends upon the desired minimum diameter of the curved ends in the deployed device. The closer the locking segments are to the device ends, the smaller the resulting diameter of the curved proximal and distal ends. Following implantation, locking segments 84, 86 maintain the respective distal and proximal tensioning strings 80, 82 in a taut state to hold the ends of device 10 in a curved, rigid shape.

Figure 17:
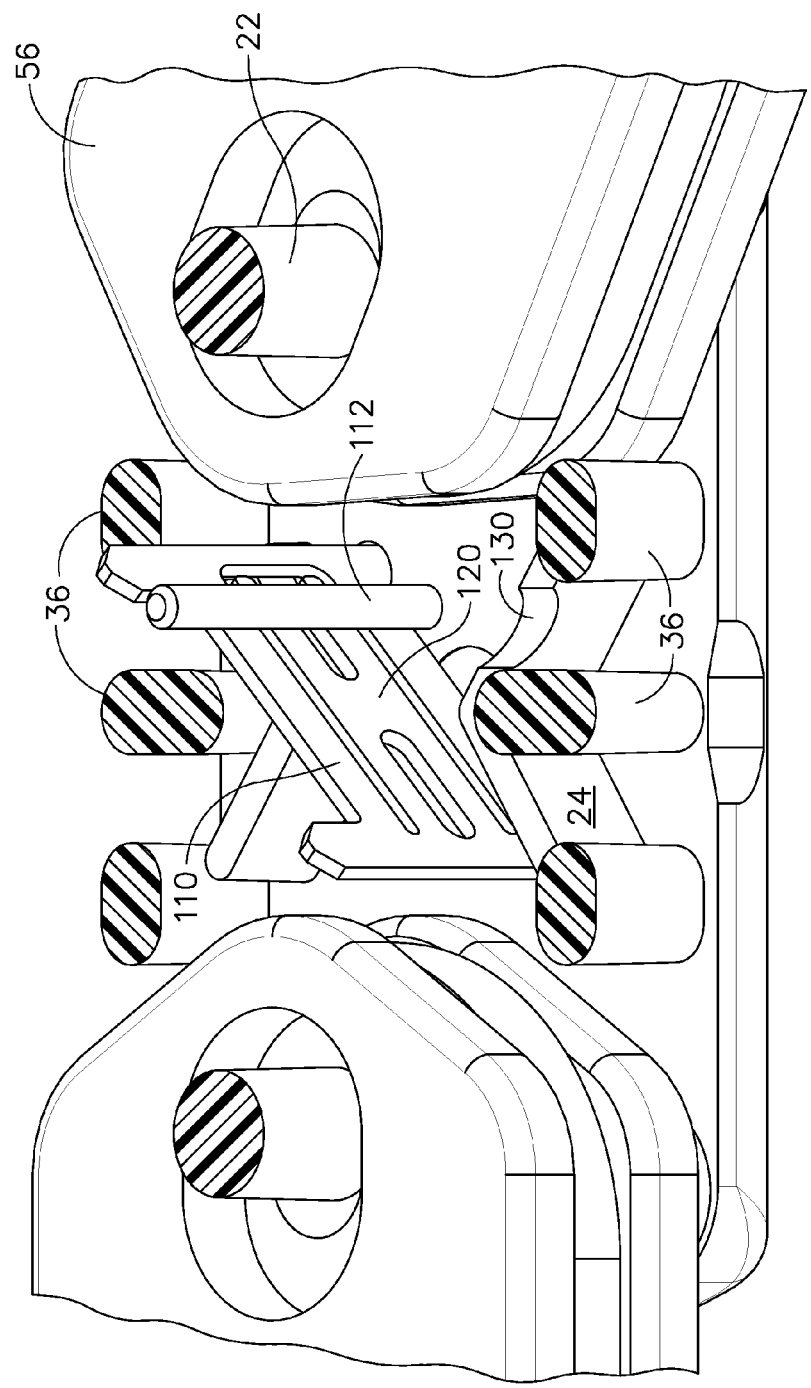
FIG. 17 is an isometric view of the proximal locking segment with the upper component removed to show the elements of the locking segment.
Figure 18:
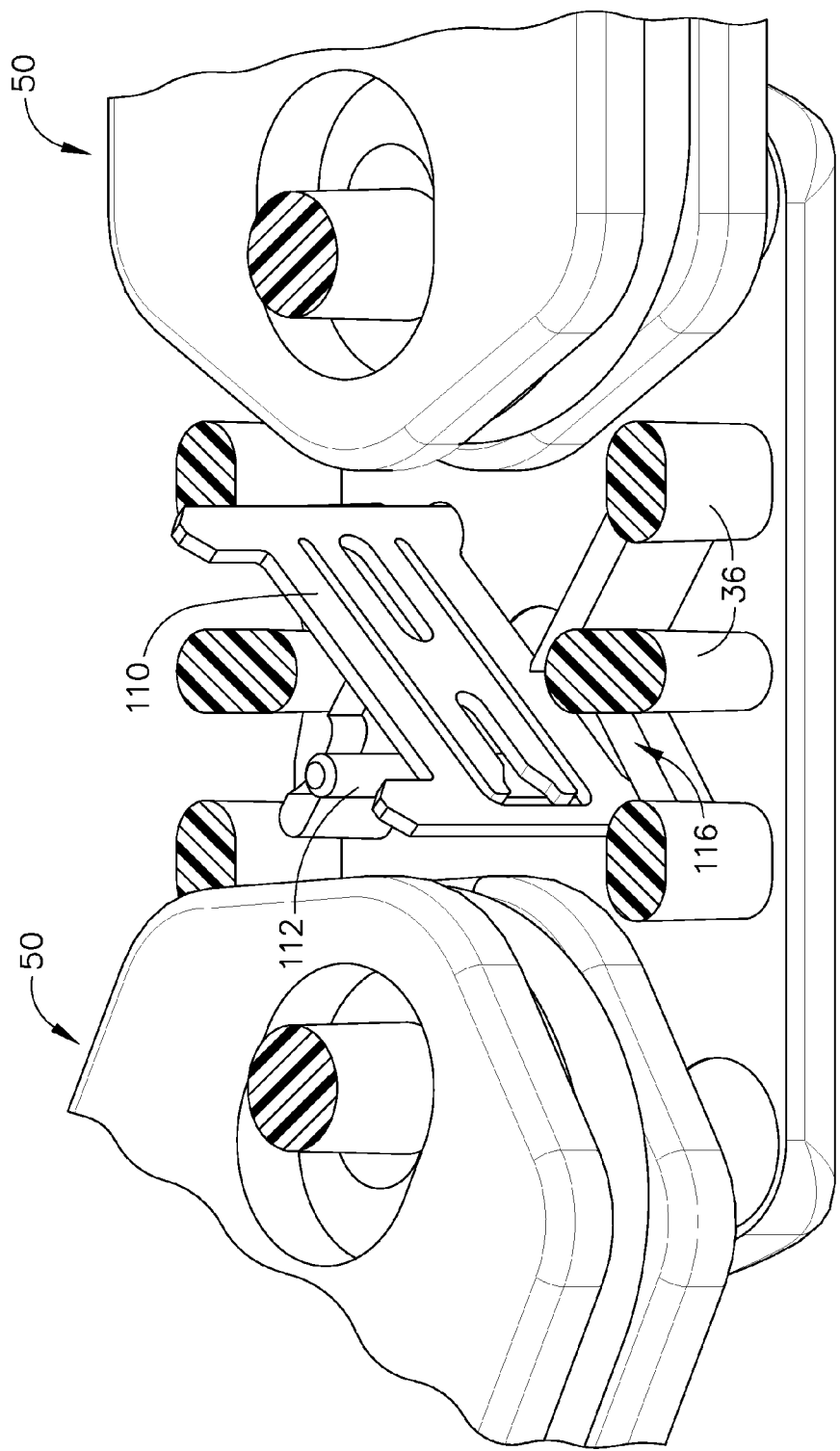
FIG. 18 is an isometric view of the proximal locking segment, similar to FIG. 17, with the locking segment shown from the opposite side.

An exemplary locking segment for the first embodiment is shown in FIGS. 17 and 18. In these Figures, the segment is shown with the upper component removed to reveal the locking elements inside the segment. The Figures show locking segment 86, which is positioned in the proximal section of the implant device. The distal section locking segment 84 would contain the same locking elements as the proximal locking segment 86, but the arrangement of the elements would be reversed to allow the tensioning string to wind in the opposite direction through the segment. Locking segments 84, 86 are similar in shape and size to the other segments 12, with the addition of several elements for securing the locking feature, such as knot 92, within the segment. To form a locking segment, a regular segment 12 is modified to include a locking piece 110 and a locking rod 112, both comprised of a biocompatible material such as, for example, stainless steel, or another similar, suitable material. Locking piece 110, shown in isolation in FIG. 19, includes opposing sets of posts 114. Posts 114 are assembled into holes 300 (shown in FIG. 20), formed into the inner surfaces of segment components 20, 30, to secure the locking piece within the modified segment. A portion of a rib 24 in the modified segment is milled off, as indicated by reference numeral 116 in FIG. 18, to allow passage of flex arm 120.

Figure 19:
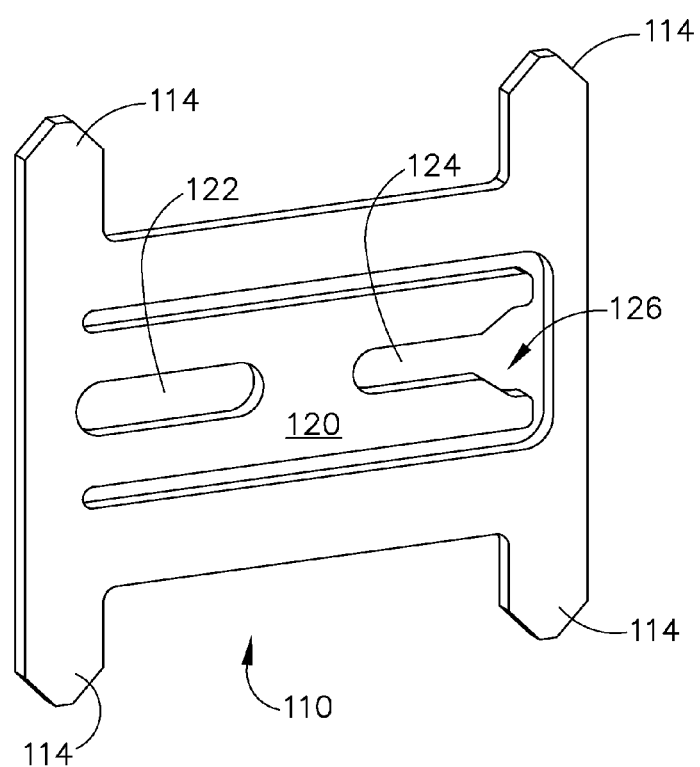
FIG. 19 is an isometric view showing the locking piece in isolation.

As shown in FIG. 19, a flexible arm 120 is formed in piece 110 by cutting a small gap substantially about the center of the locking piece. Arm 120 remains attached to piece 110 along one side to allow the arm to flex relative to the piece. Flexible arm 120 includes a pair of slots 122, 124. Slots 122, 124 provide for passage of the tensioning string through arm 120 as the string is pulled through the locking segment during deployment. An enlarged area 126 is provided into slot 124 at the tip of arm 120 to allow knot 92 to pull through the arm during tensioning. Locking rod 112 is secured at opposite ends within holes formed in the segment components 20, 30. Locking rod 112 is mounted next to the unattached tip of arm 120 and extends perpendicular to the bending angle of the arm. Locking rod 112 blocks arm 120 from bending in the direction of the pin during and following deployment.

Figure 20:
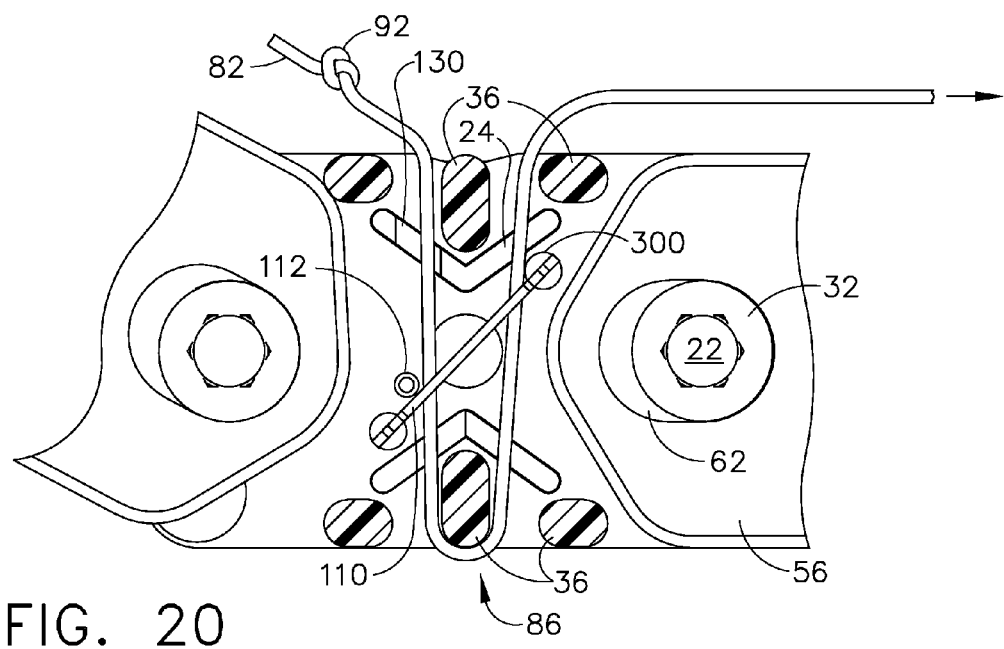
FIG. 20 is a top view showing the string routing through the locking segment prior to the knot entering the segment.

As shown in FIG. 20, tensioning string 82 extends from the proximal member end into the locking segment 86 through an opening between the posts of bracket 36. Within locking segment 86, the string passes through slot 124 in piece 110. A small arc 130 is milled out of a rib 24 to provide a pathway for the string and locking knot to pass to piece 110. Just before slot 124, the tensioning string passes locking rod 112. From slot 124, the tensioning string extends around the back of bracket 36 at the far side of the segment. From the back of bracket 36, the string runs forward through the second slot 122 in piece 110. From piece 110, the string passes between a different set of bracket posts 36 and exits the segment on the same side that the string entered.

Figure 22:
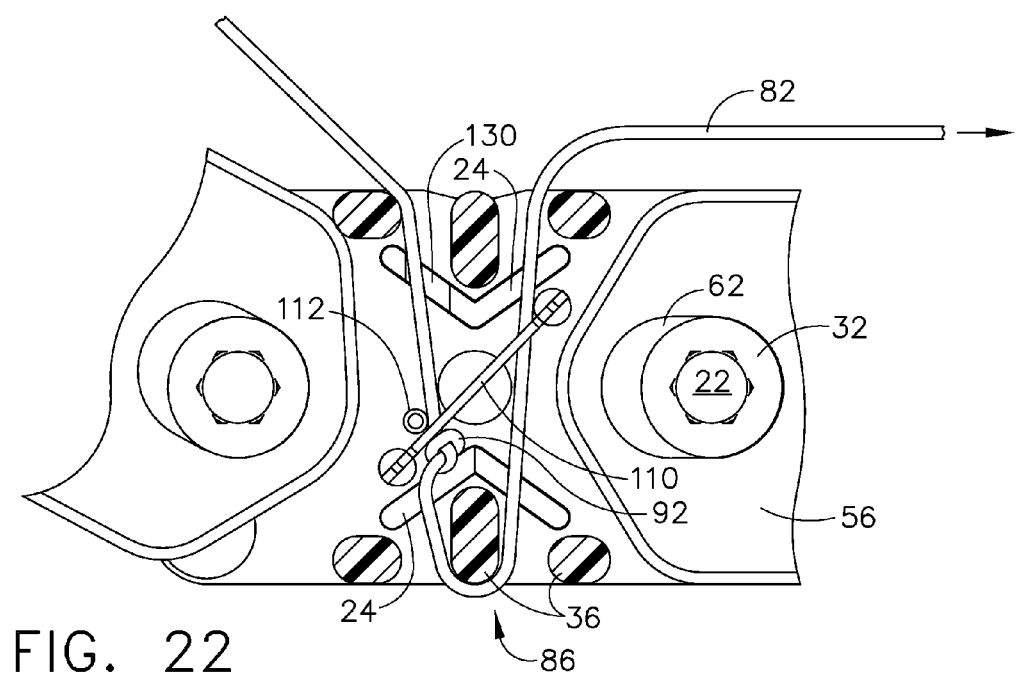
FIG. 22 is a top view showing the string routing through the locking segment with the knot retained by the locking piece and rod.
Figure 21:
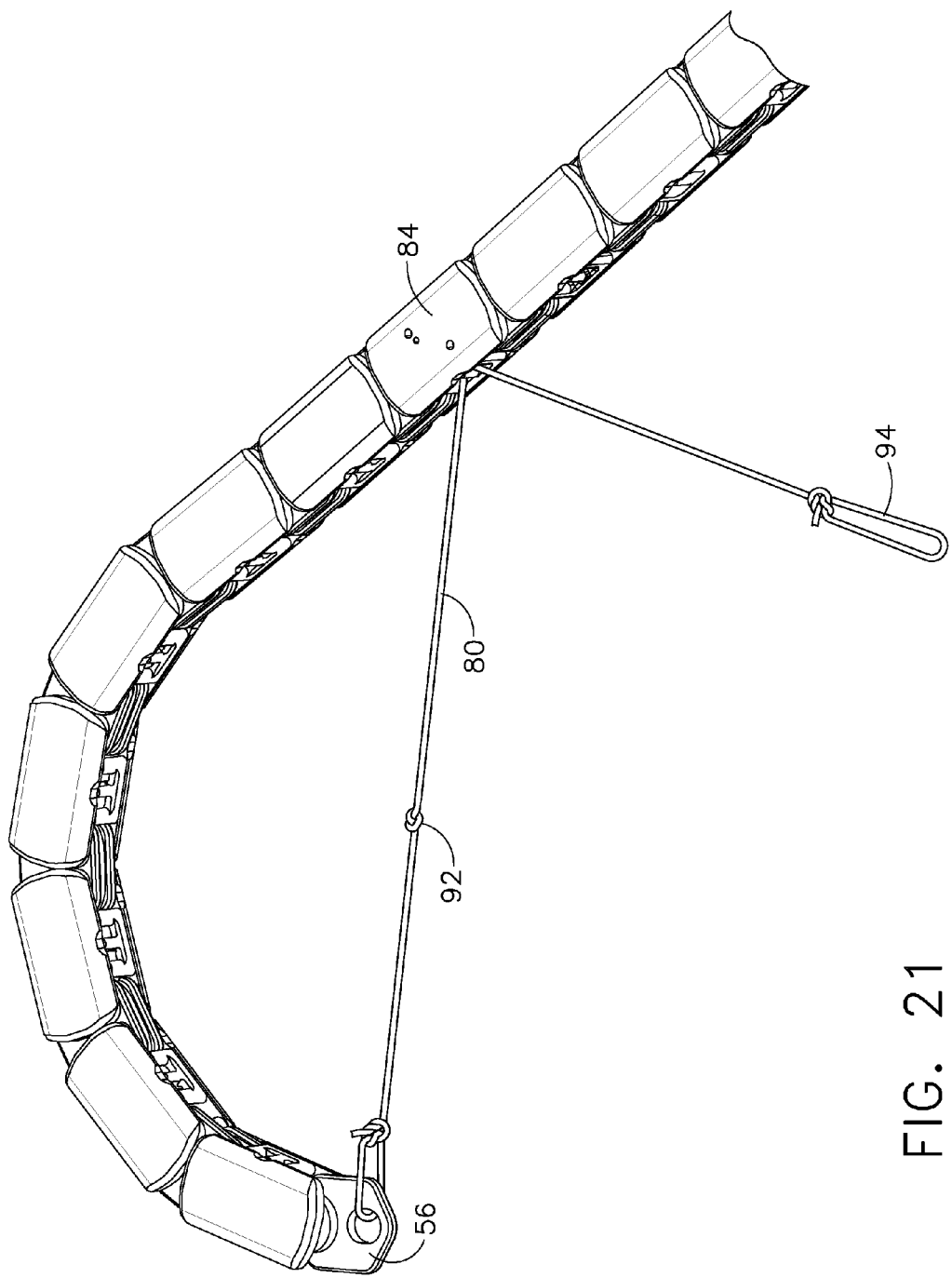
FIG. 21 is an isometric view of the distal segment section showing the string pulled to flex the segments into a partially deployed configuration.

During implantation, a pulling force is applied to the tensioning strings to tighten the strings and flex the segments at the ends of the implant member, as shown in FIG. 21 for the distal end of the implant member. As each string is pulled during implantation, the string moves through the respective locking segment 84, 86 via the routing described above. Initially, the string moves freely through the locking segment as the pulling force of the string begins to draw segments 12 and linking assemblies 50 into a curvilinear shape. As the tension on the string continues, and the member end nears the desired curve diameter, the rate of resistance to bending between adjacent segments increases. When the member end reaches the desired curve diameter, locking knot 92 on the string is drawn towards and eventually into the locking segment, as shown in FIG. 20. As knot 92 is pulled through the locking segment, the knot pushes against arm 120 to flex the arm outward and away from rod 112, until the arm is sufficiently flexed to allow the knot to snap through the enlarged tip of the arm. After knot 92 passes through arm 120, the arm swings back into contact with rod 112, locking the knot on the far side of arm 120, as shown in FIG. 22. Rod 112 prevents arm 120 from swinging back open and releasing knot 92 when a reverse pulling force is applied to the tensioning string. Retaining knot 92 on the far side of locking piece 110 maintains the tensioning string in a taut condition, thereby holding the end of the implant member in a stiff, curved configuration.

FIGS. 20 and 22 show locking segment 86 for locking the proximal tensioning member 82 in a taut, deployed state. However, it should be understood that the distal locking segment 84 and tensioning string 80 operate in substantially the same manner to draw and hold the distal end segments in a curved configuration. Locking segments 84, 86 are substantially the same, with only the position of the locking elements being switched, so that with both locking segments the tensioning string can enter the locking segment through an opening closer to the end of the implant member, and exit the locking segment through an opening closer to the midpoint of the member.

As implant member 14 is flexed, disks 52 in the linking assemblies are stretched between the pivot bosses 32. The elastic quality of disks 52 causes the disks to resist flexing, and thereby produce an outward force tending to straighten the implant member. When the disks are fixed into a stretched configuration, by locking knots 92 inside locking segments 84, 86, the disks produce a rigid condition within the curved member ends. This rigid condition resists deformation of the curved ends and applies an outward force against the walls of the cavity.

Figure 23:
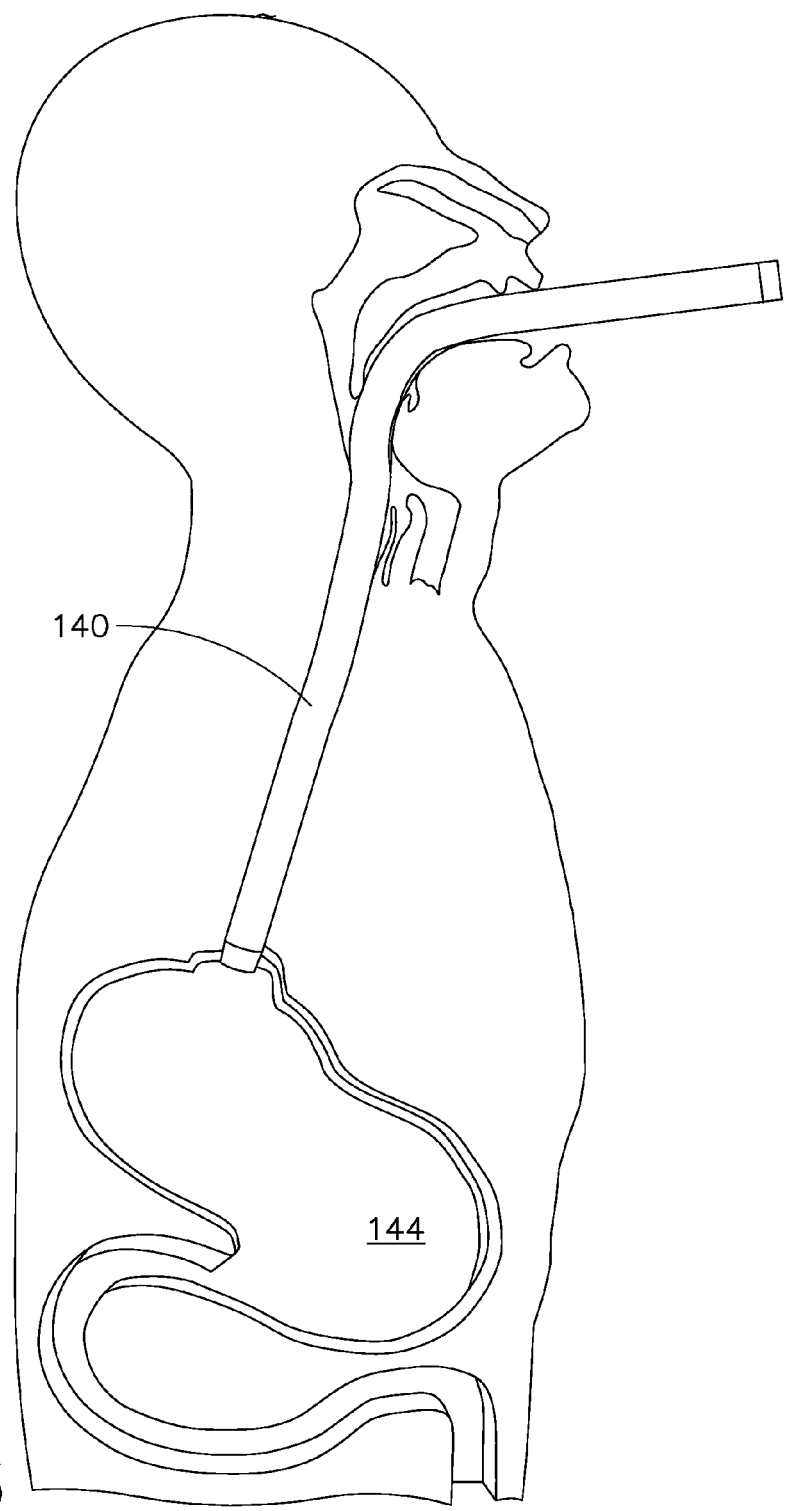
FIG. 23 depicts an endoscopy overtube placed in the esophagus.

In the preferred method of the invention, device 10 is delivered into the gastric cavity in an undeployed, substantially linear shape. To implant device 10, an overtube 140, shown in FIG. 23, is initially inserted into the esophagus. With overtube 140 in place, an endoscope is passed transesophageally into the gastric cavity 144 to assess the interior surfaces of the cavity and determine a placement location for the device. A guide wire (not shown) may be used if necessary to reinsert the endoscope with overtube 140.

Figure 24:
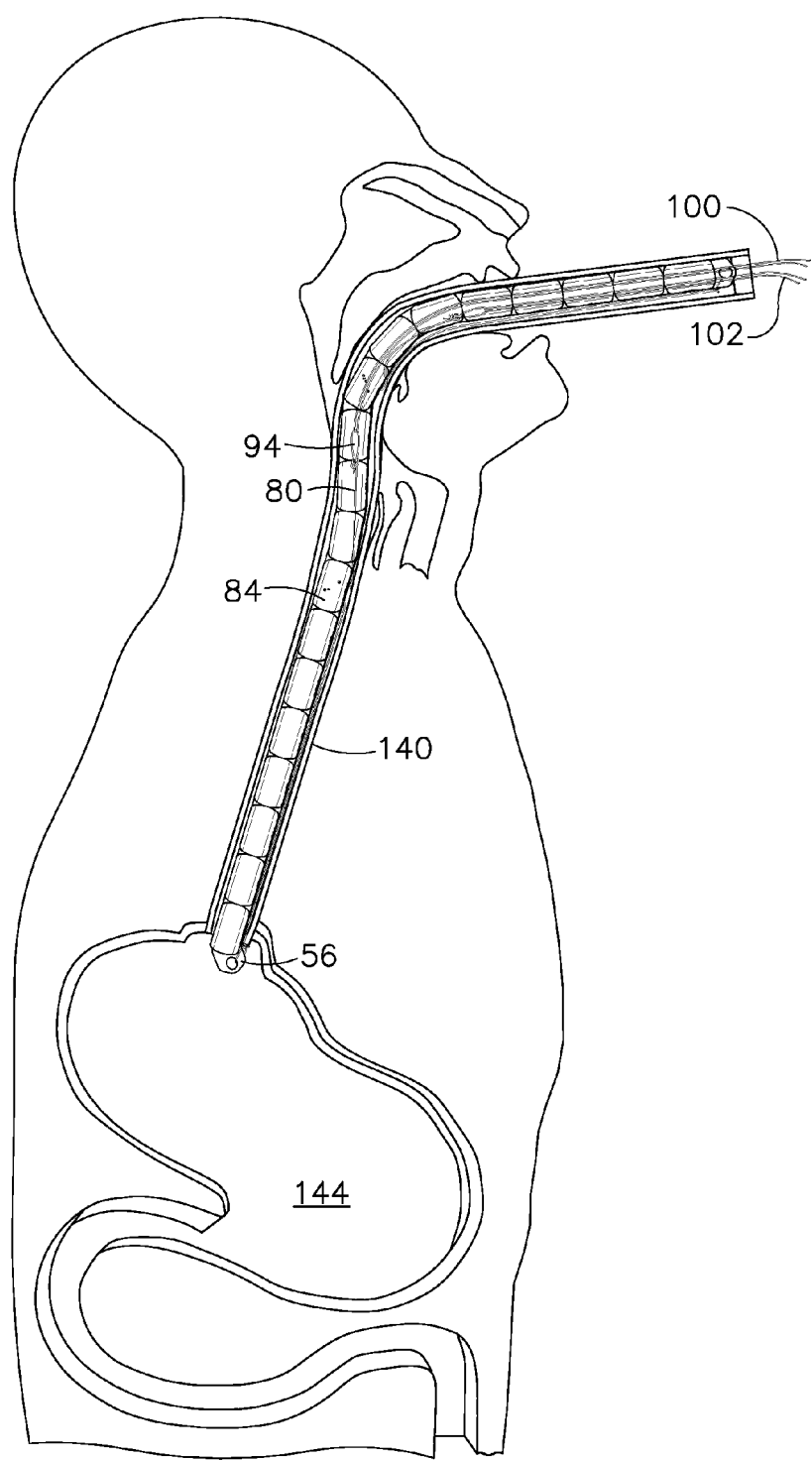
FIG. 24 depicts an implant device being delivered through the overtube.
Figure 25:
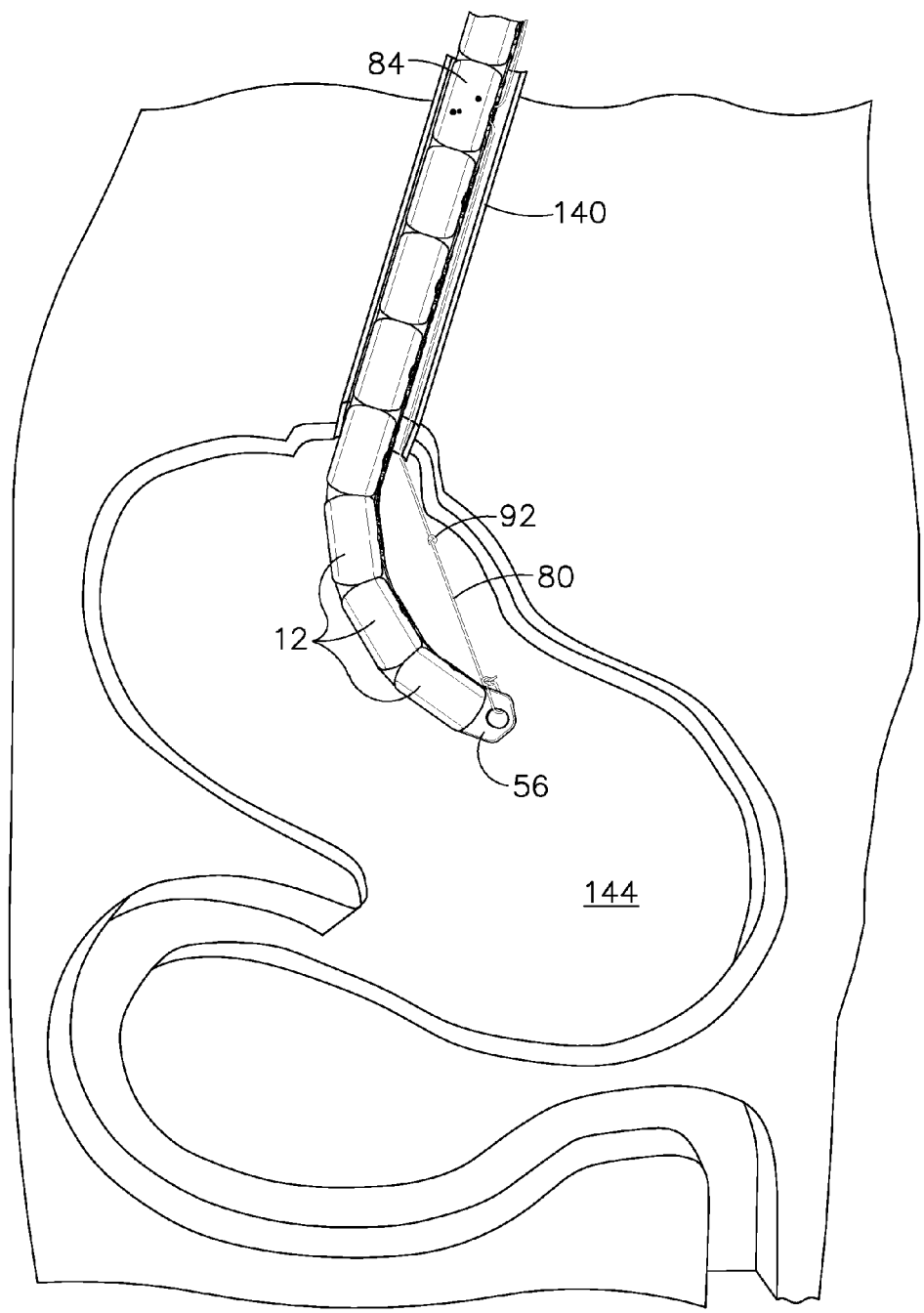
FIG. 25 depicts the deployment sequence with the first three segments just entering the gastric cavity and tension being placed on the pull cable.
Figure 26:
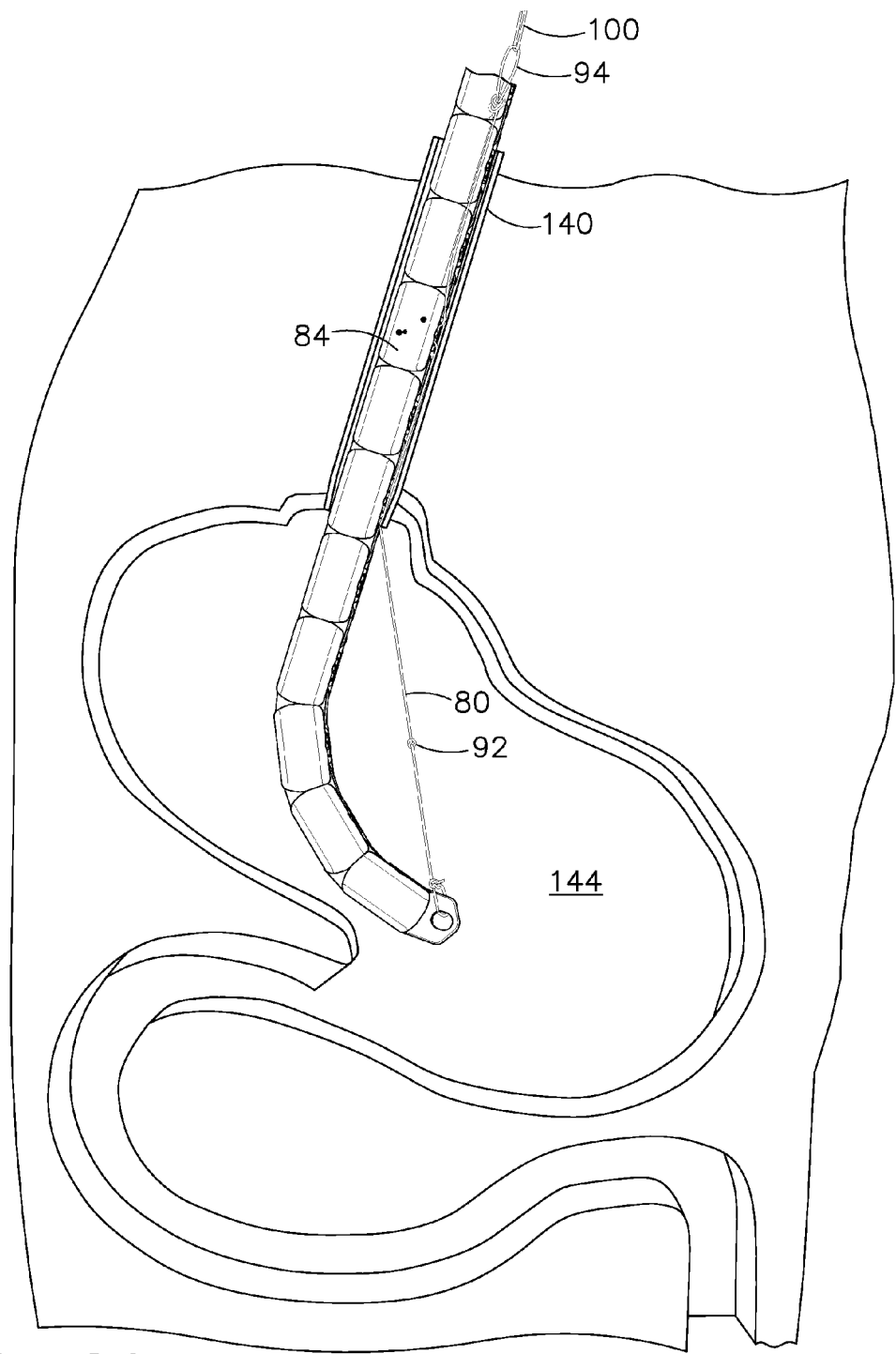
FIG. 26 depicts the deployment sequence with the first five segments inside the gastric cavity, and tension being placed on the pull cable.

After the desired location is determined, the endoscope is removed, and the distal end of device 10 is inserted into overtube 140. Device 10 is passed through overtube 140, as shown in FIG. 24, until the distal end enters the gastric cavity 144. A grasper 152 may be operated through the working channel of the endoscope to assist in pushing the device through overtube 140. While the grasper holds onto the proximal end of the device, pressure can be applied to the grasper to push the device through the overtube. To maneuver through overtube 140, segments 12 flex both within plane, about pivot bosses 32, and also out of plane, as linking assemblies 50 shift within the gap between segment components 20, 30. After three or four segments of implant member 14 have entered gastric cavity 144, tension is applied to distal pull cable 100 from outside of the body using pull block 104. The force on pull cable 100 dislodges tapes 90 to pull distal tensioning string 80 out of attachment against the side of implant member 14, and tightens the string between the distal link end 56 and locking segment 84, as shown in FIG. 25. As additional links are gently advanced into gastric cavity 144, distal tensioning string 80 continues to be pulled taut through locking segment 84, flexing segments 12 as the segments emerge from overtube 140 into the gastric cavity. The distal end segments are delivered into cavity 144 in the direction of the pylorus, so that when fully implanted device 10 at least partially blocks the pylorus. The location of the string openings in locking segment 84 causes the distal device end to curve inward towards the center of gastric cavity 144 as the tensioning string is drawn through the locking segment. As tensioning string 80 is drawn taut, the string moves back through overtube 140 due to the connection between the string loop 94 and pull cable 100, as shown in FIG. 26.

Figure 27:
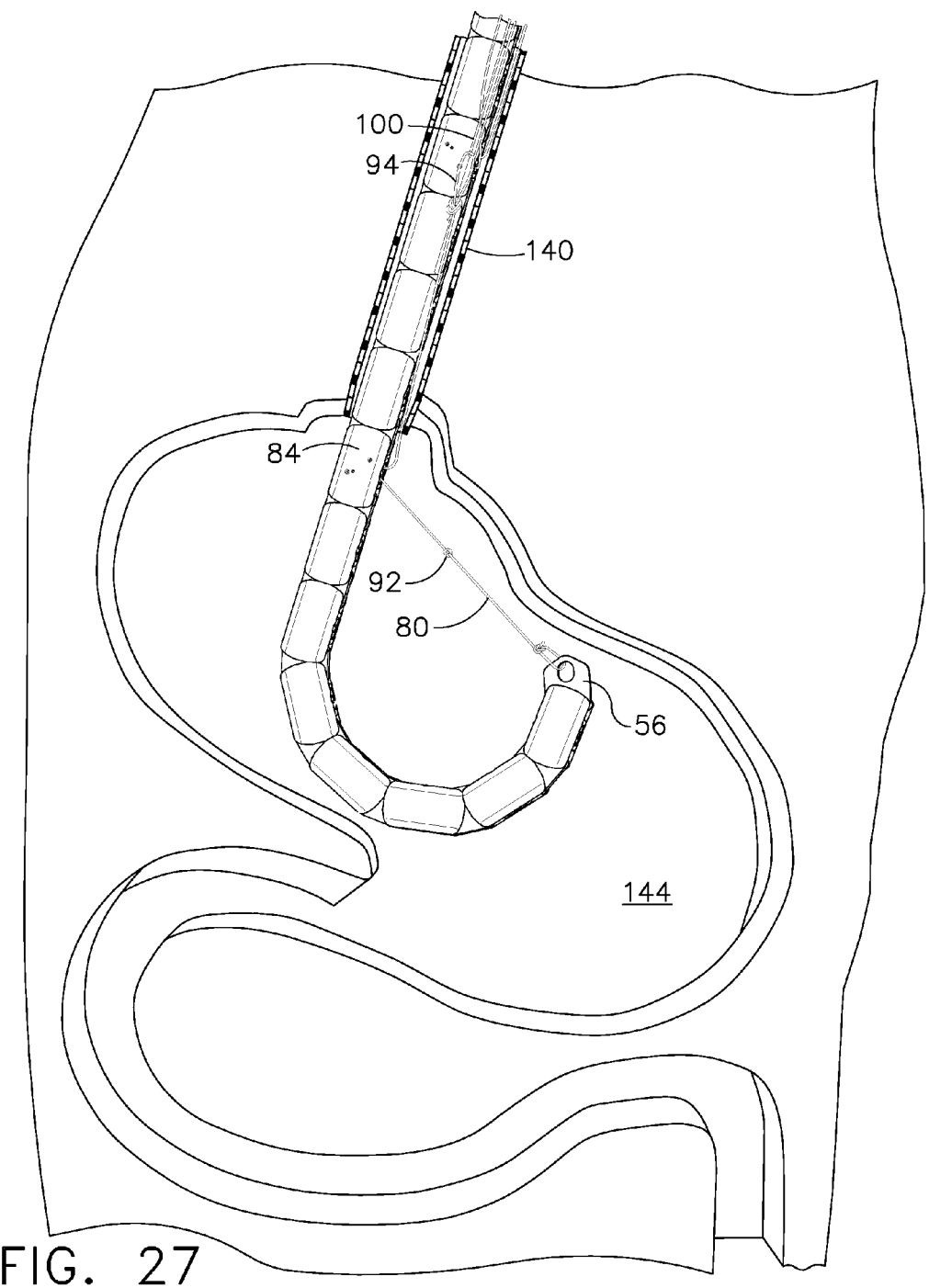
FIG. 27 depicts the deployment sequence with the first eight links entering the gastric cavity and tension being placed on the pull cable to draw the knot closer to the locking segment.
Figure 28:
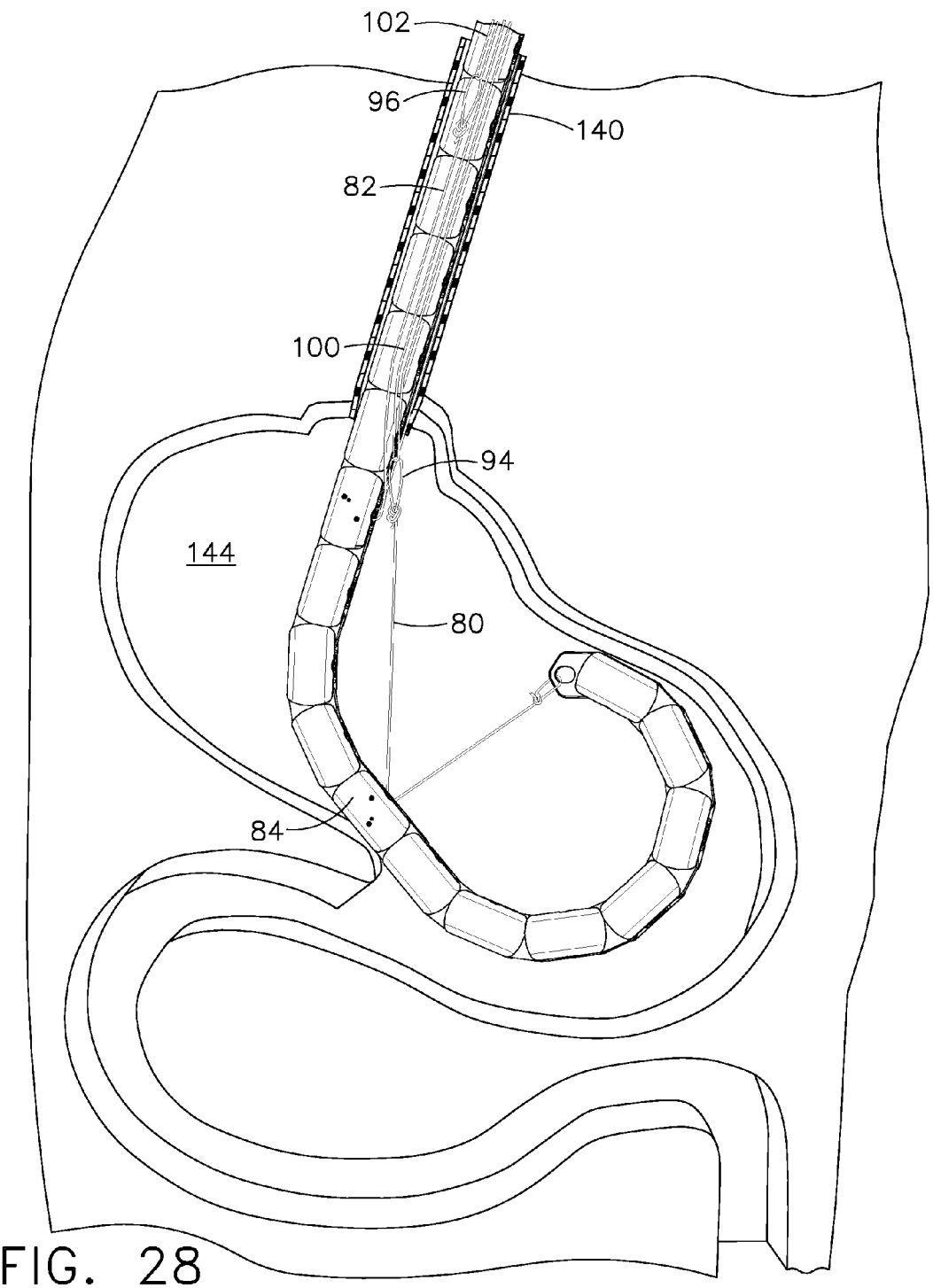
FIG. 28 depicts the deployment sequence with the first twelve links entering the gastric cavity and tension being applied to the pull cable to lock the distal knot inside the locking segment.

Inside locking segment 84, the advancing tensioning string 80 slides through rib arc 130 and slots 122, 124 in flexible arm 120. Tension continues to be applied to distal pull cable 100, flexing the distal end of implant member 14, as distal locking segment 84 enters gastric cavity 144. With distal locking segment 84 inside cavity 144, pull cable 100 continues to be drawn back through overtube 140, as shown in FIG. 27, until locking knot 92 on distal tensioning string 80 is pulled inside distal locking segment 84 (FIG. 28). As locking knot 92 moves through locking segment 84, the knot pushes against flexible arm 120 to bend the arm out of the path of the advancing knot. The knot snaps through the enlarged tip of arm 120 and locks on the far side of the arm, as described above. The knot 92 is prevented from retracting back through locking segment 84 by locking rod 112. With knot 92 retained inside locking segment 84, the distal end of the implant member is fixed in a curved, outwardly biased configuration and the bending resistance of the member end is substantially increased.

As knot 92 is advancing into locking segment 84, the center section of implant member 14 continues to gently move into gastric cavity 144. As the center segments advance, distal pull cable 100 continues to be pulled taut to assure that the distal curved end advances and situates as desired inside the cavity. Pull cable 100 can be used to guide placement of device 10 as additional segments continue to emerge into the cavity. Preferably, the distal end of implant member 14 is guided into a position in the fundic region of the gastric cavity.

Figure 29:
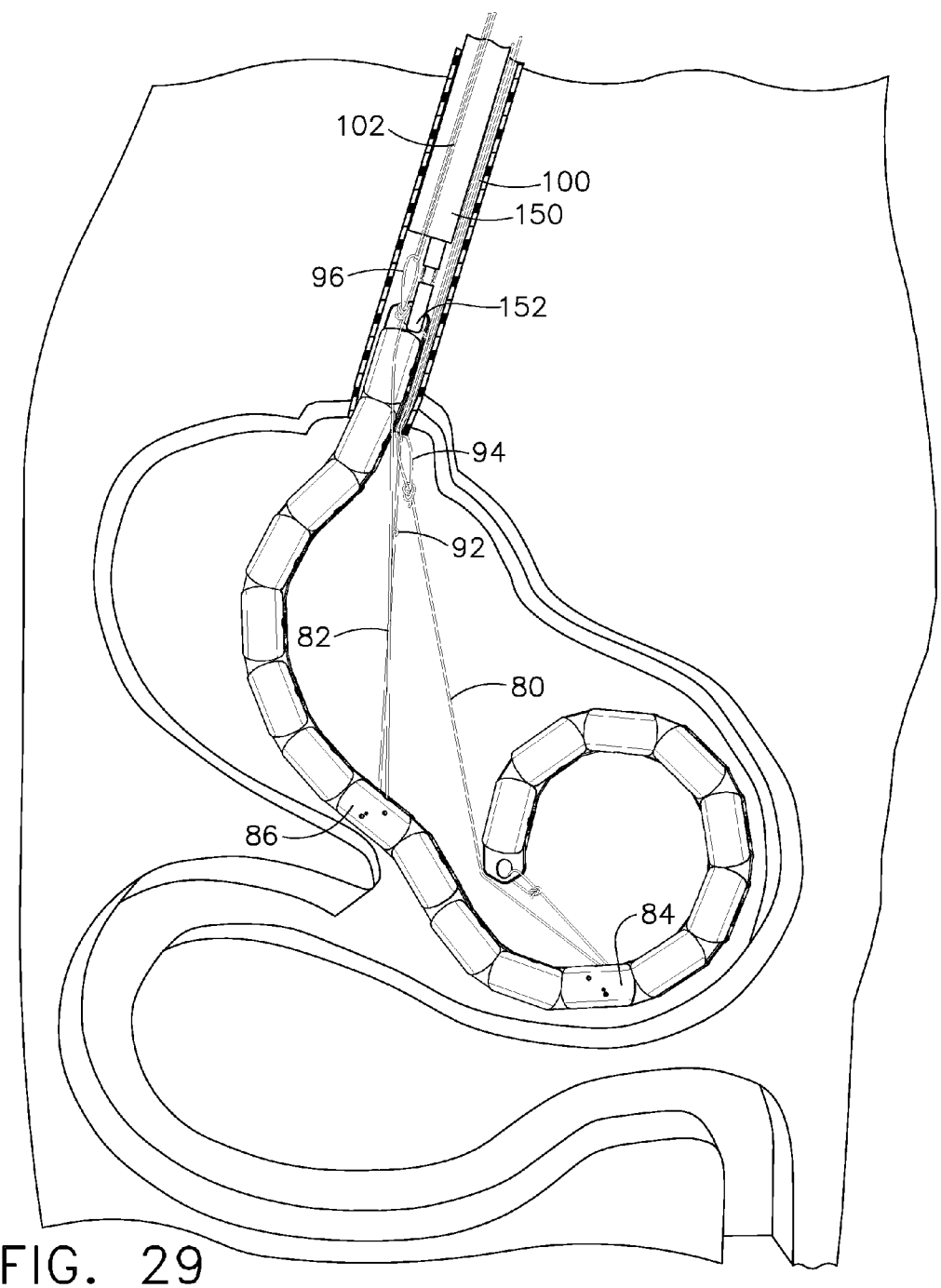
FIG. 29 depicts the deployment sequence with the first seventeen links entering the gastric cavity and tension being placed on the proximal pull cable to hold the implant member in place while a flexible endoscope advances the remaining segments into the cavity.
Figure 30:
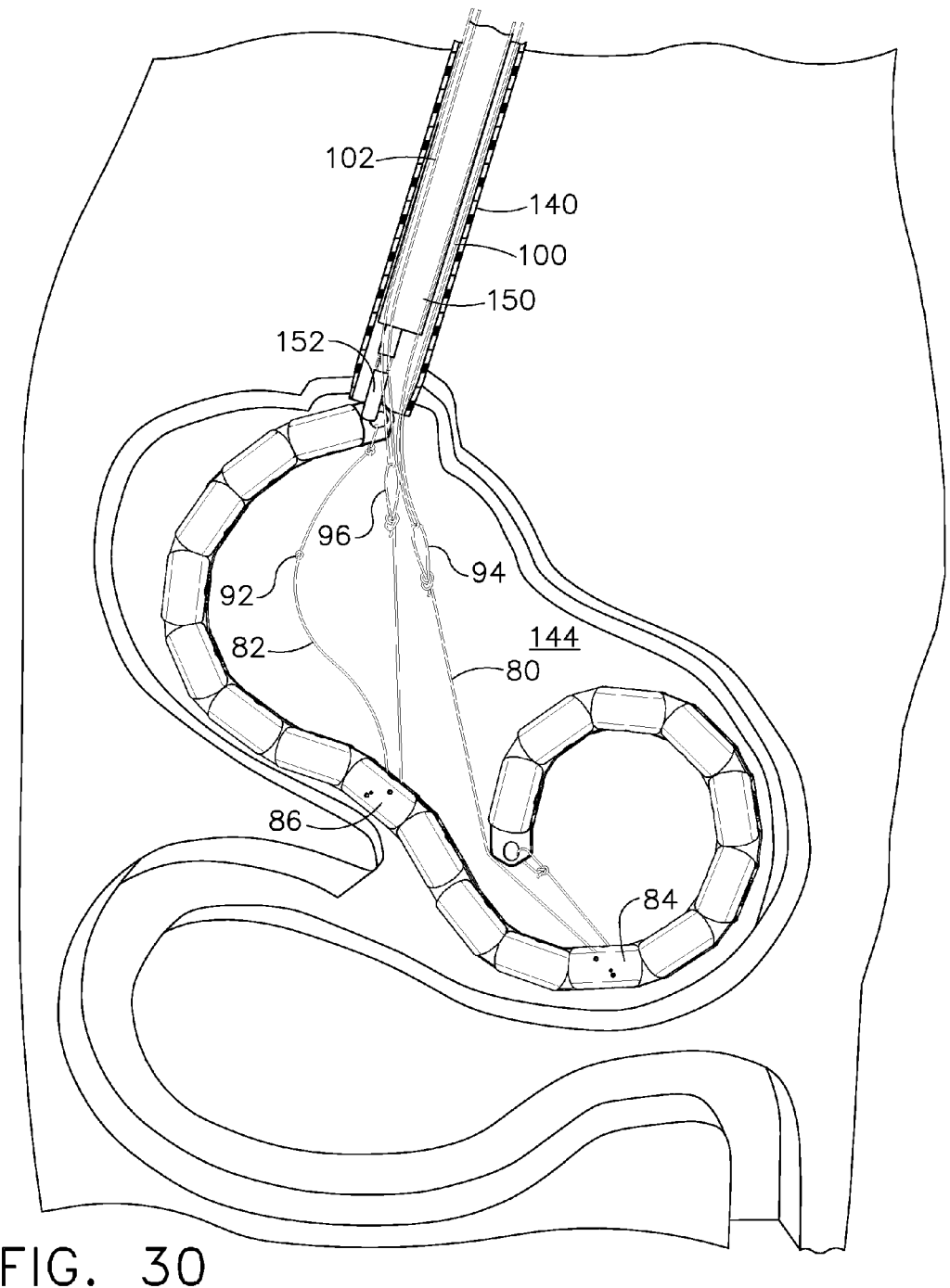
FIG. 30 depicts the deployment sequence with the entire device entering the gastric cavity.
Figure 31:
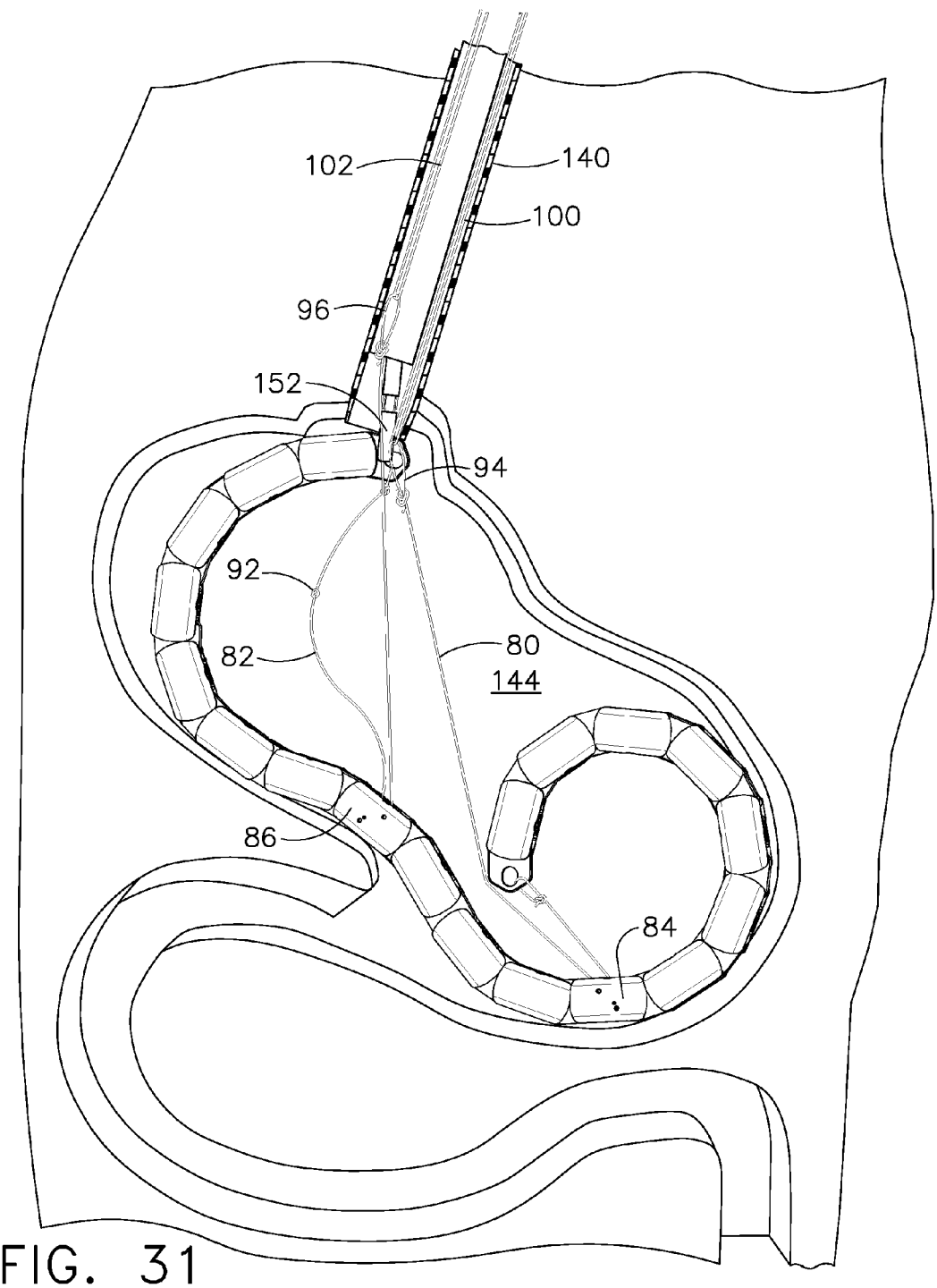
FIG. 31 depicts the deployment sequence with the entire device entering the gastric cavity and the pull cables being drawn up the overtube.

As delivery of device 10 continues, proximal locking segment 86 emerges into the interior of gastric cavity 144, followed by the proximal segment section (i.e. segments between the proximal locking segment and proximal end of the device). During delivery of the proximal section of device 10, tension is applied to proximal pull cable 102 (via pull block 106) to draw the proximal segments into an arc as the segments advance into the stomach. As the proximal segments are pushed into gastric cavity 144 by a grasper 152, the segments apply outward pressure along the greater curve of the cavity, as shown in FIG. 29. The outward pressure against the cavity wall allows the remaining proximal segments to be delivered and deployed within the cavity, as shown in FIGS. 30 and 31.

Figure 32:
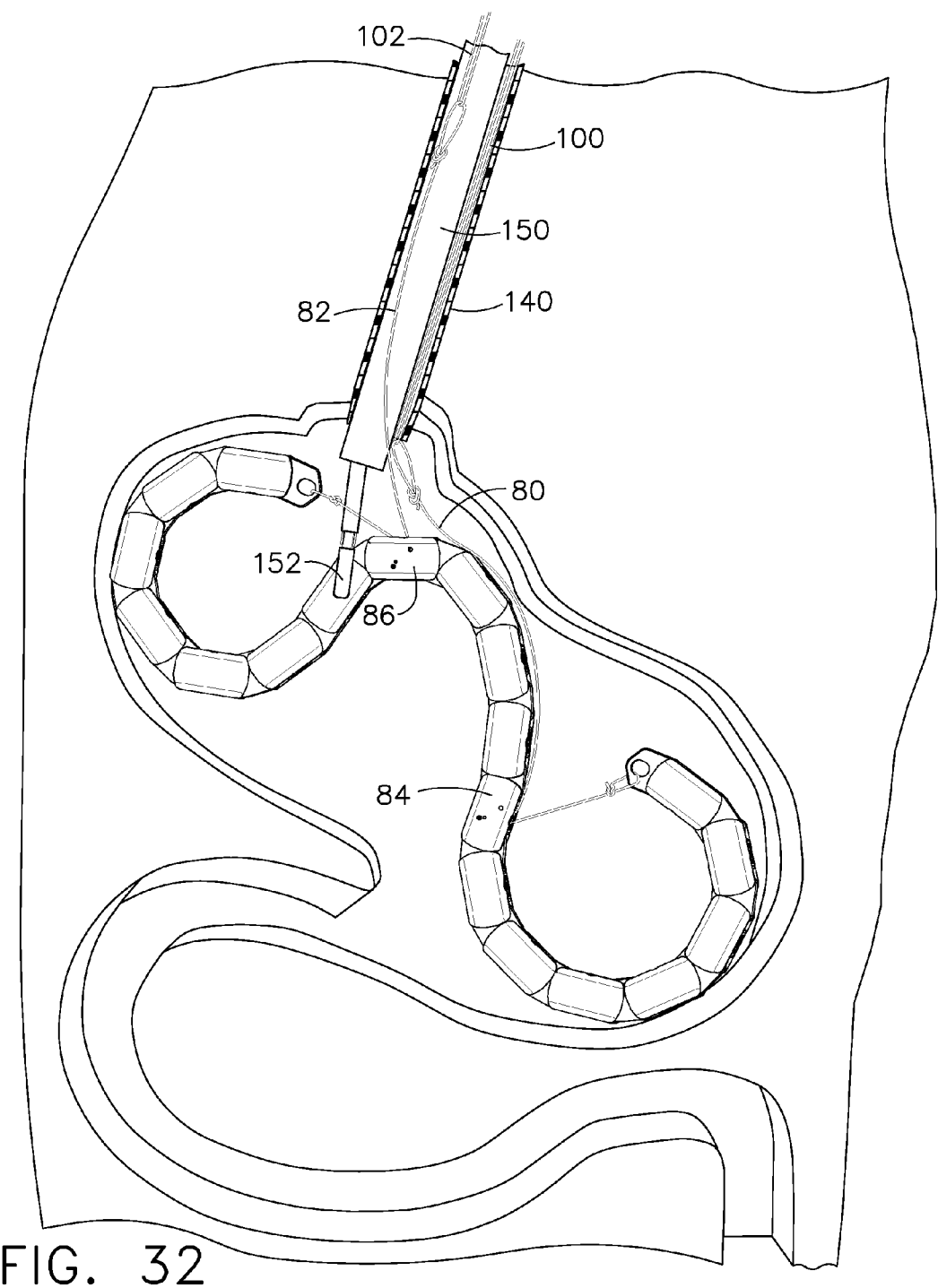
FIG. 32 depicts the deployment sequence with the entire device deployed inside the gastric cavity and the proximal string knot being locked inside the locking segment.

After the proximal end of implant member 14 has been delivered into gastric cavity 144, proximal pull cable 102 is tensioned to pull the proximal locking knot 92 into locking segment 86. Inside locking segment 86, knot 92 deflects arm 120 out of the path of the advancing knot, as described above, until the knot snaps into a locked position on the far side of the arm. As pull cables 100, 102 are being pulled to lock knot 92 in locking segment 86, the cables temporarily pull the center segments away from the greater curve of the cavity, as shown in FIG. 32. With proximal knot 92 fixed inside locking segment 86, the proximal end of implant member 14 is also locked in a rigid, curved configuration. With knots 92 fixed inside locking segments 84, 86, segments 12 in both the distal and proximal sections are bent into arcs having at least the minimum diameter required to prevent migration of the device from the gastric cavity.

Figure 33:
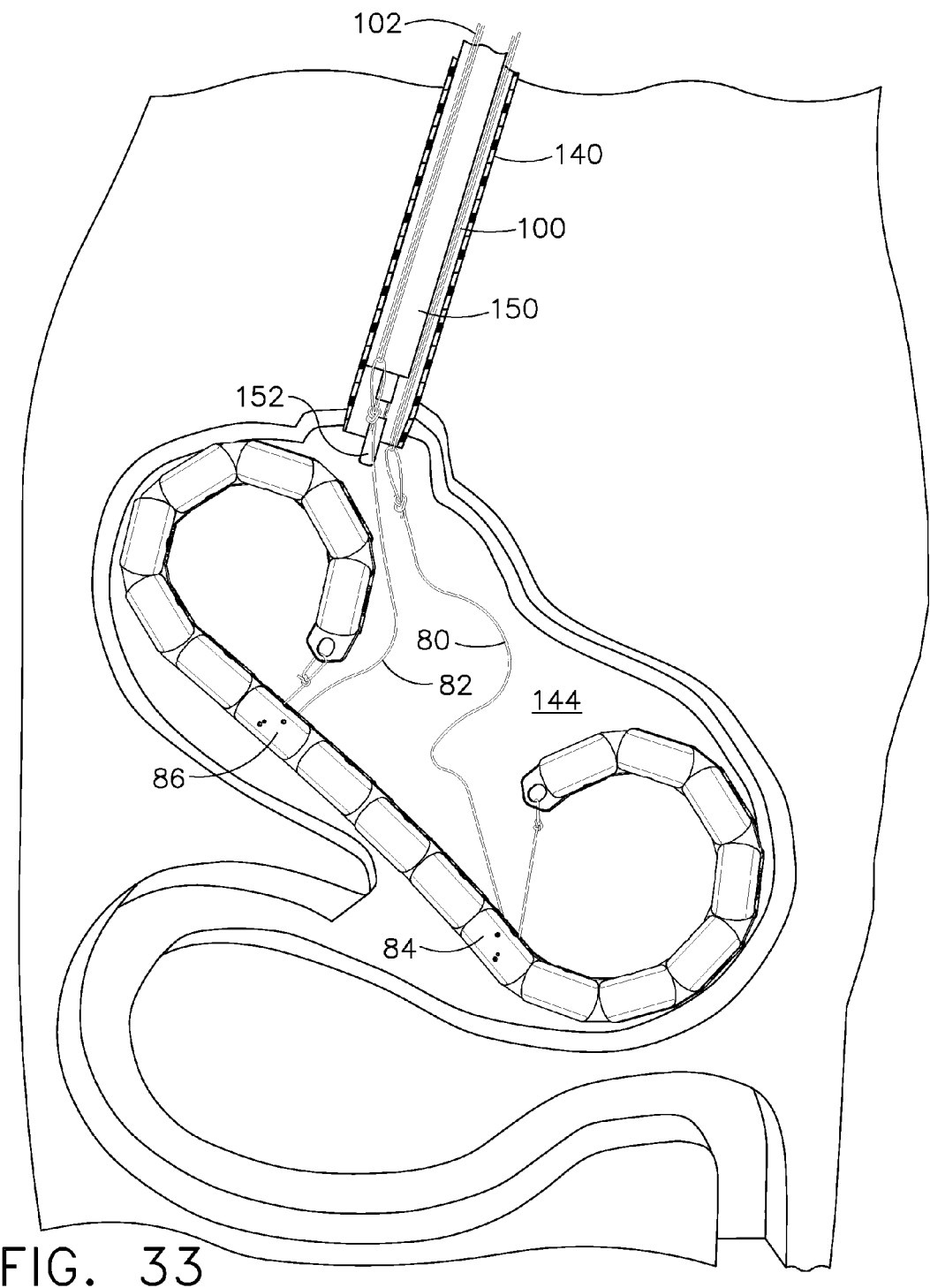
FIG. 33 depicts the deployment sequence with the entire device deployed inside the gastric cavity and the endoscope inspecting the placement of the device.
Figure 34:
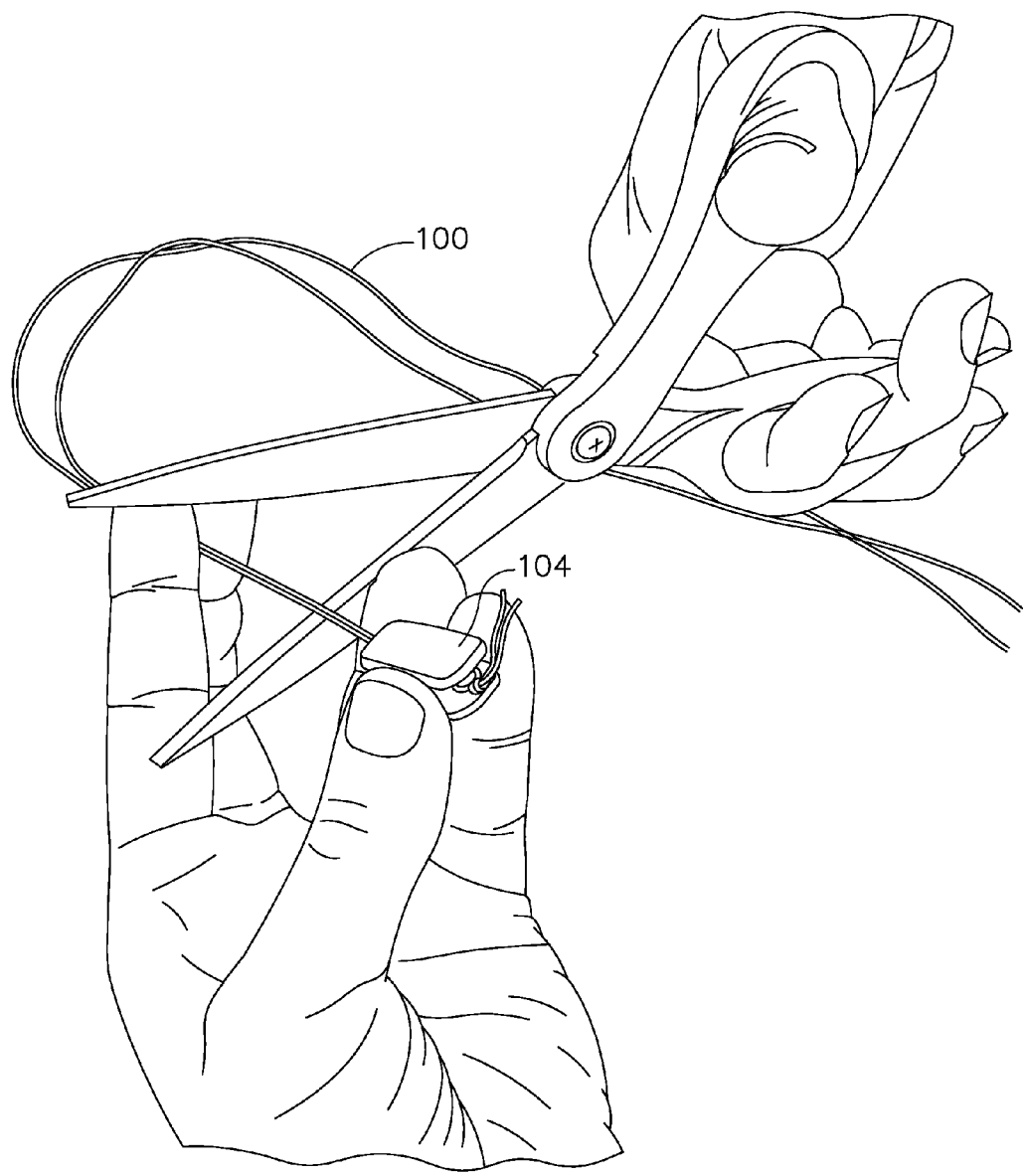
FIG. 34 depicts the distal pull cable being cut so that the pull cable can be removed from the device.
Figure 35:
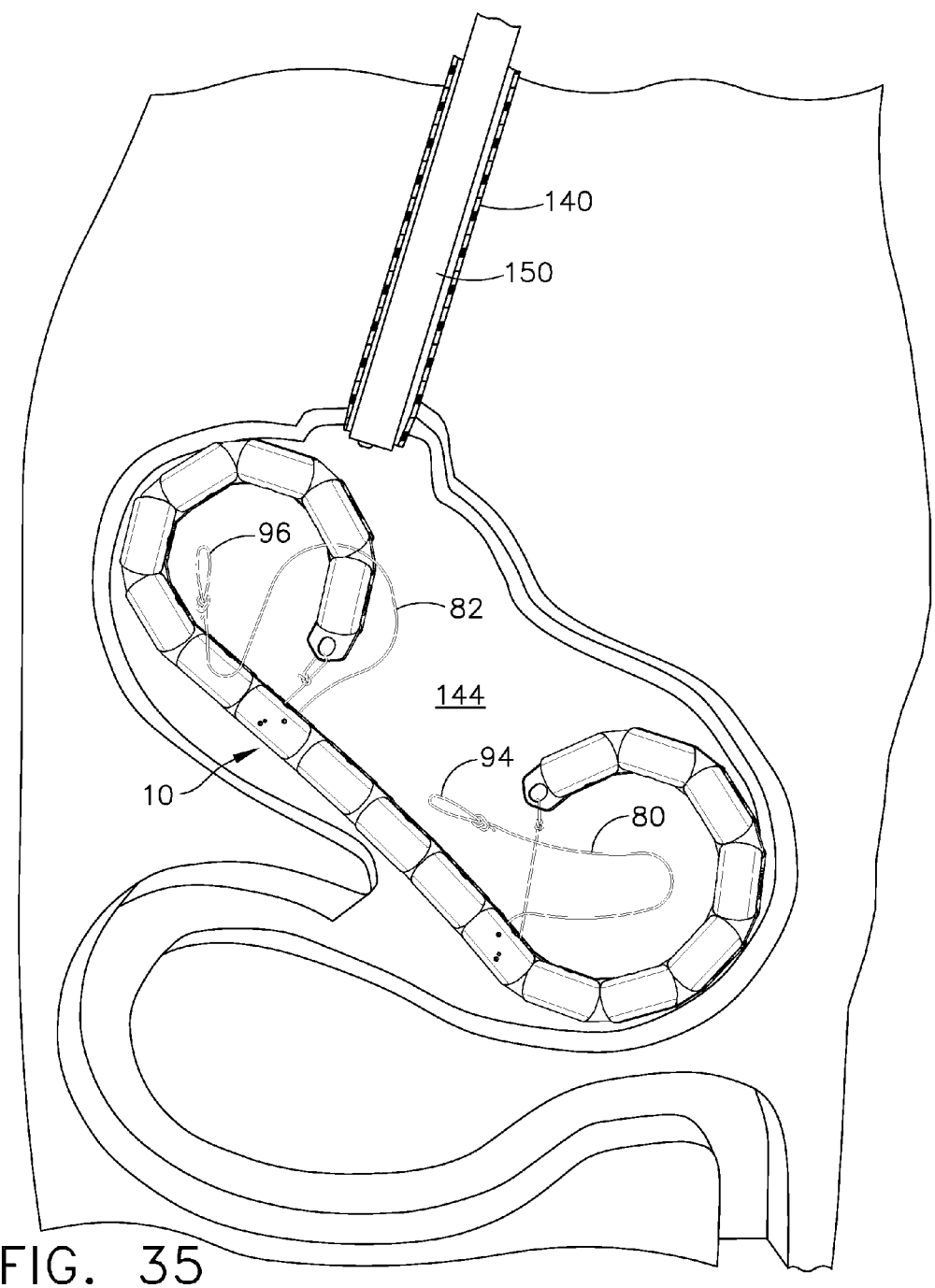
FIG. 35 depicts the resultant device configuration within the gastric cavity after the proximal and distal pull cables are both cut and removed from the cavity.

After the proximal member end is locked into a curved configuration, the placement of implant device 10 within gastric cavity 144 can be inspected using endoscope 150, as shown in FIG. 33. Once the proper placement is determined through endoscope 150, graspers 152 is removed from the working channel of the endoscope. With the implant device fully deployed, pull cables 100, 102 are removed from the distal and proximal pull loops 94, 96 by cutting the cables adjacent to pull blocks 104, 106, as shown in FIG. 34 for the distal pull cable 100. After the pull cables are severed, the cables are pulled out of tensioning string loops 94, 96 and back through overtube 140, leaving the deployed implant member and tensioning strings inside the gastric cavity. A final inspection can be done with endoscope 150 following removal of the pull cables, as shown in FIG. 35.

Figure 36:
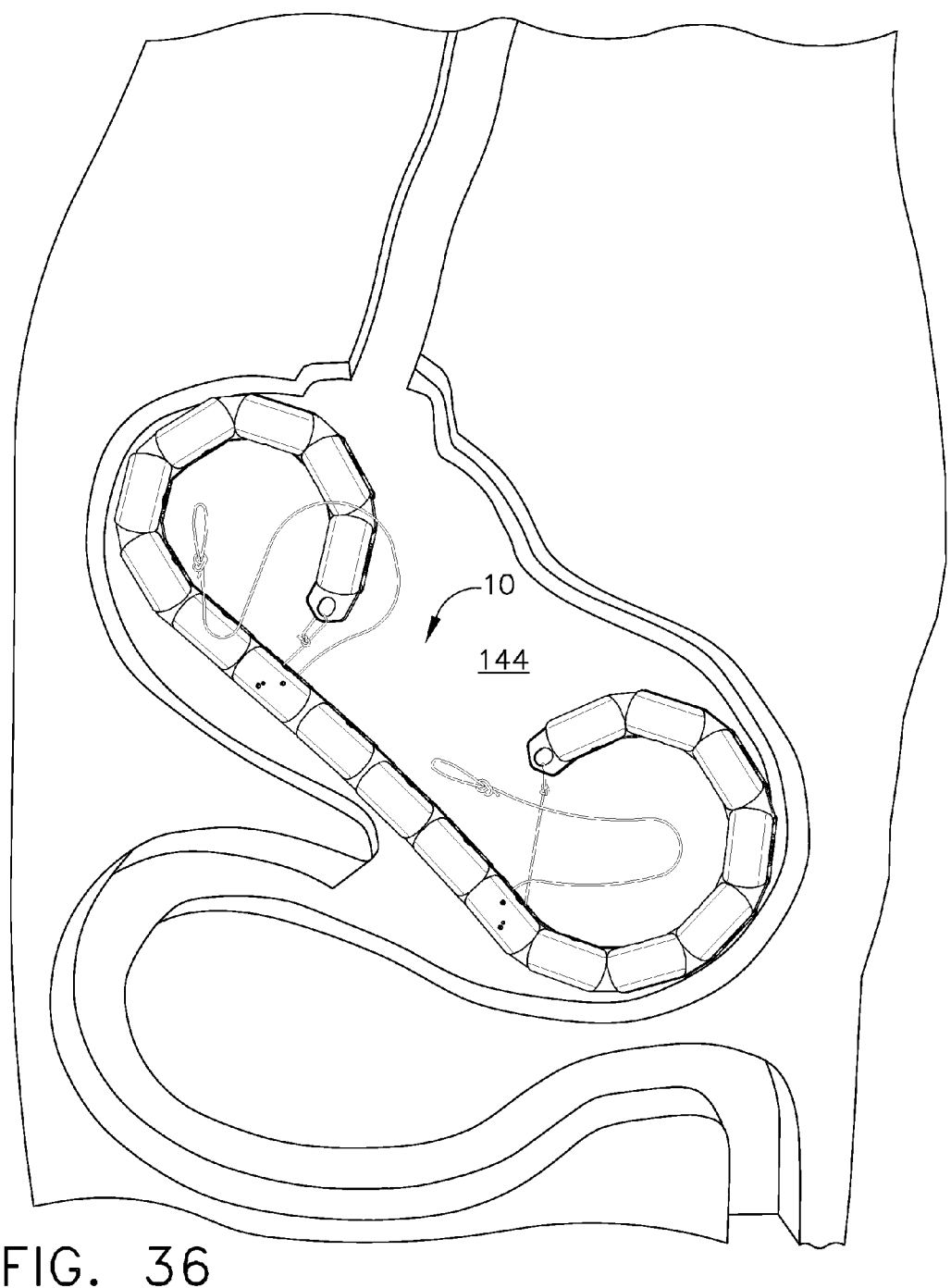
FIG. 36 depicts the resultant device configuration within the gastric cavity after the pull cables, endoscope and overtube are removed.

FIG. 36 depicts device 10 in a deployed configuration following implantation inside the gastric cavity. In the deployed configuration, device 10 is flexible enough to allow some compression and movement relative to the stomach mucosa, preventing erosion, but rigid enough to prevent unwanted buckling and proximal or distal migration. The geometry of the curved member ends is larger than the pylorus to prevent migration of the device through the pylorus over time. Erosion may be further minimized through optimal material selections, exterior shapes that vary pressures on the lumen walls, and exterior shapes that encourage movement of the device within the stomach so that no single location is always subject to the same contact loads from the device.

Figure 37:
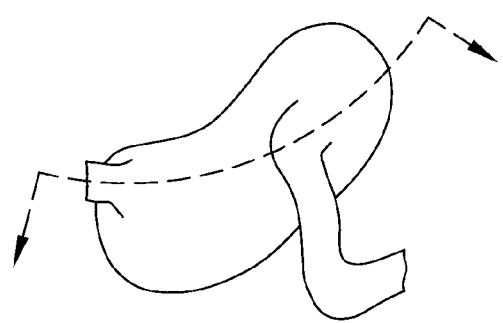
FIG. 37 is a side view of a gastric cavity prior to deployment of an implant device.
Figure 38:
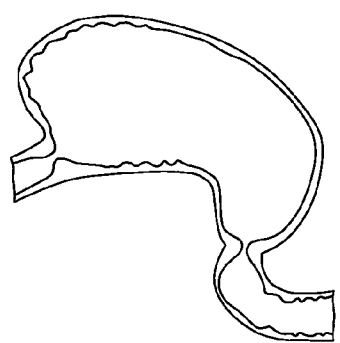
FIG. 38 is a cross-sectional view of a gastric cavity prior to deployment of an implant device.
Figures 39, 40:
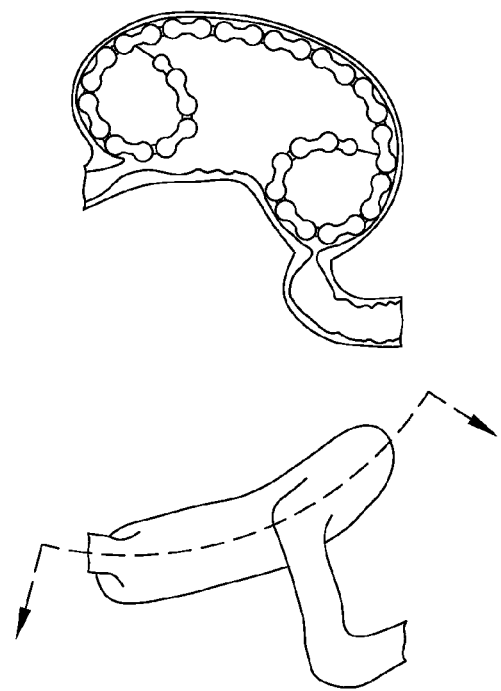
FIG. 39 is a side view of a gastric cavity showing a flattened cavity after implant device deployment.
FIG. 40 is a cross-sectional view of a gastric cavity showing cavity extension in the plane of the device following deployment of a representative implant device.

FIG. 37 shows the exterior shape of the gastric cavity in an unaltered state prior to deployment of the implant device. FIG. 38 shows a cross-sectional view of the gastric cavity prior to delivery and deployment of the implant device of the invention. FIGS. 39 and 40 show the altered state of the gastric cavity following deployment of the implant device. As shown in FIG. 39, the outward force of the flexed segments acts against the greater curve of the gastric cavity to flatten the cavity by drawing the anterior and posterior walls of the cavity together. This flattening of the cavity can be noted by comparing FIG. 39 to FIG. 37. FIG. 40 shows a preferred deployment position for device 10, in which the distal end of the device is flexed into a circle in the fundus of the gastric cavity, while the proximal end of the device is flexed into a circle in the antrum of the cavity. Within the encircled ends, and along the center section of the device, the flexed segments produce an outward force that acts against the greater curve of the stomach to draw the anterior and posterior cavity walls together, and also induce a hormonal response which reduces the desire to eat.

Figure 41:
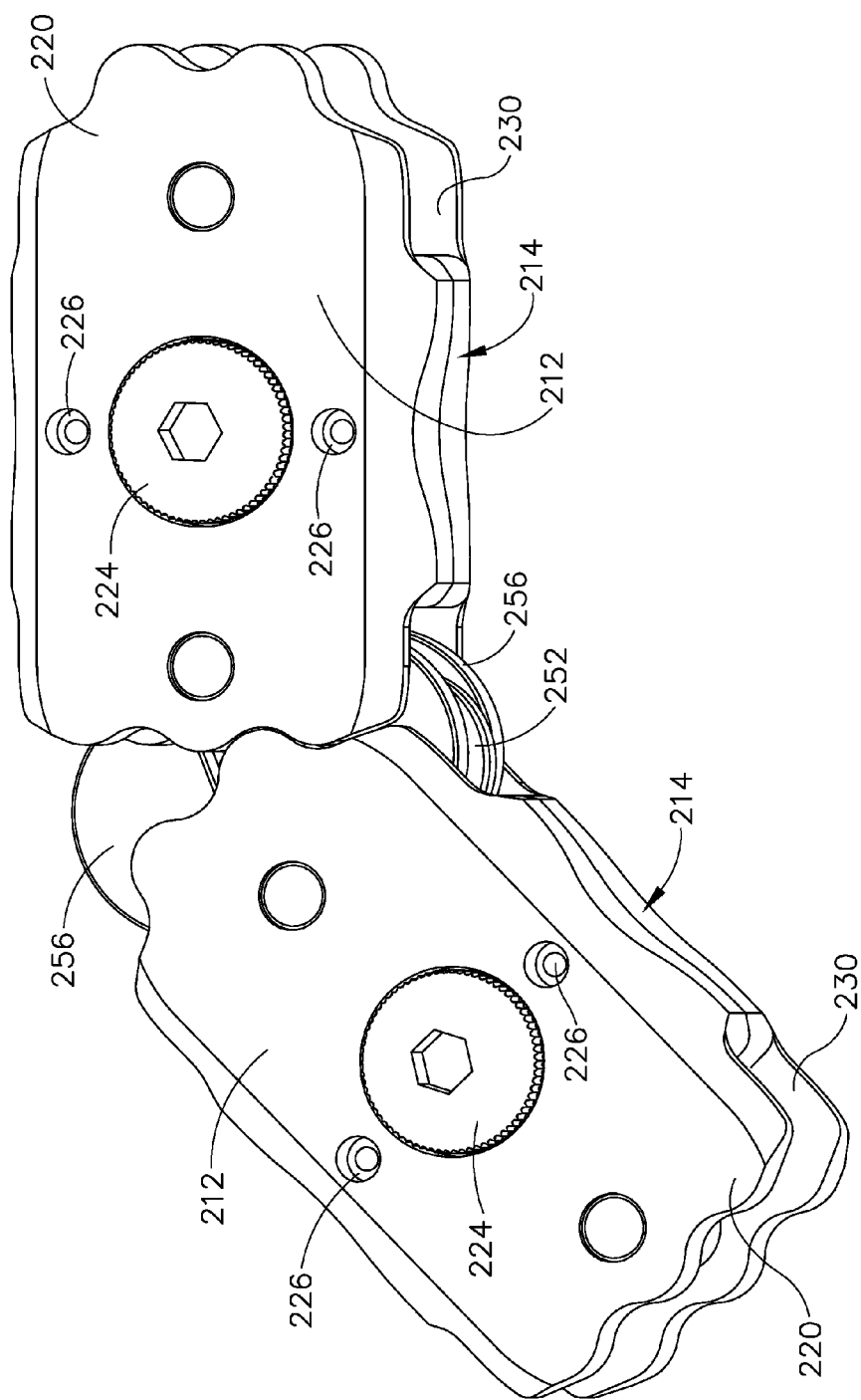
FIG. 41 is an isometric view of a second embodiment for the implant device showing a linking assembly and adjoining segments in a bent configuration.
Figure 42:
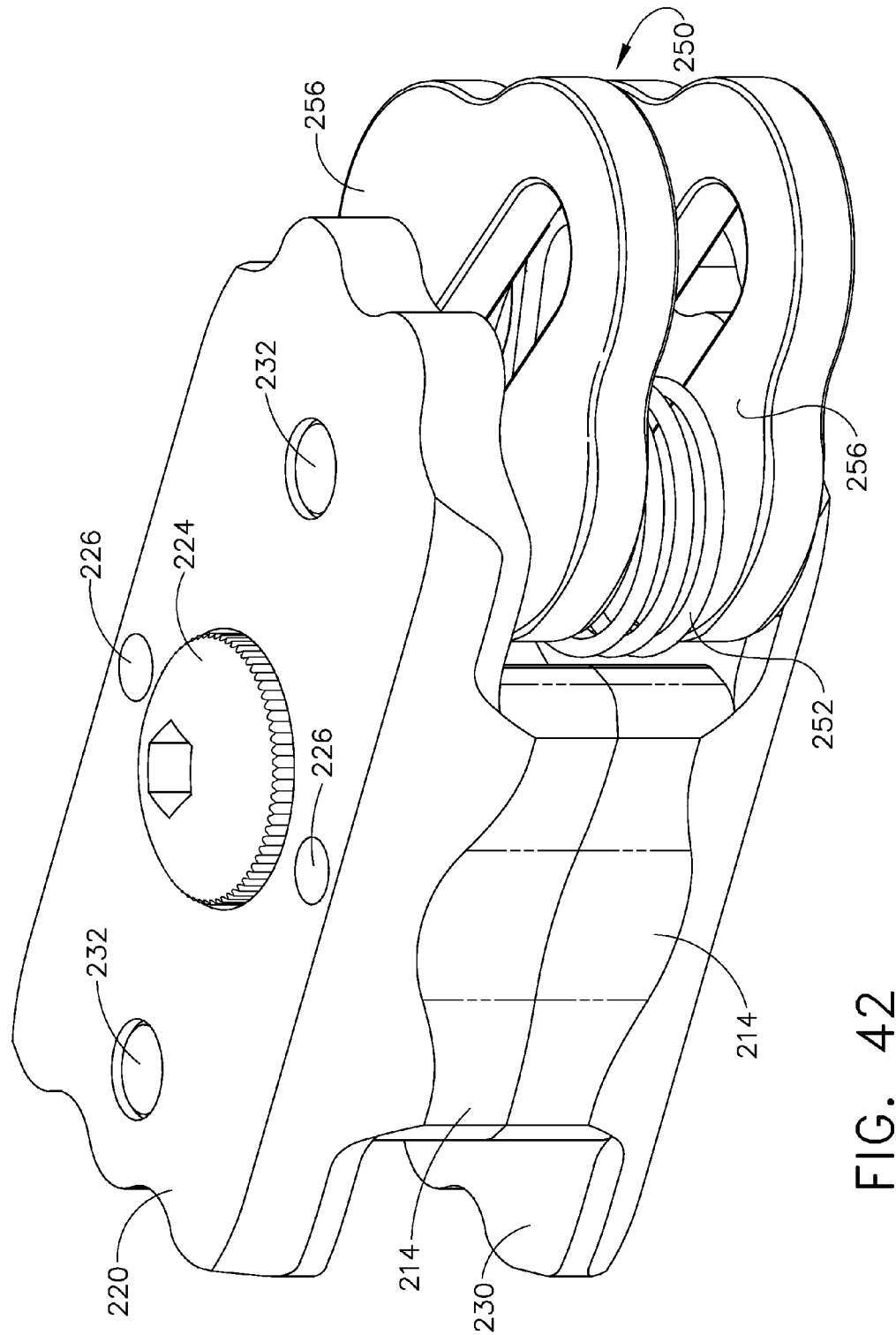
FIG. 42 is an isometric view of a single segment of the second embodiment of the implant device.
Figure 43:
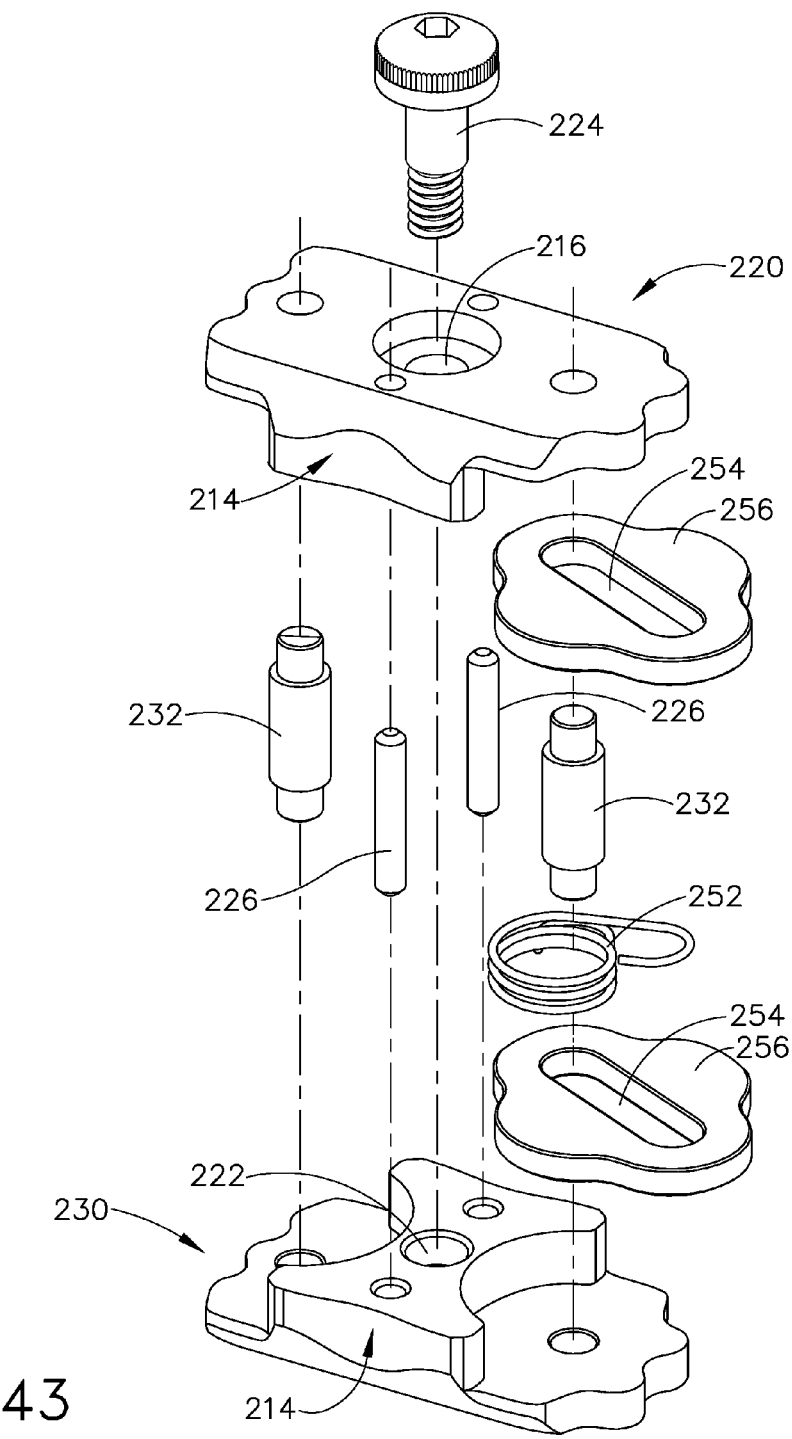
FIG. 43 is an exploded view of the segment shown in FIG. 42.
Figure 44:
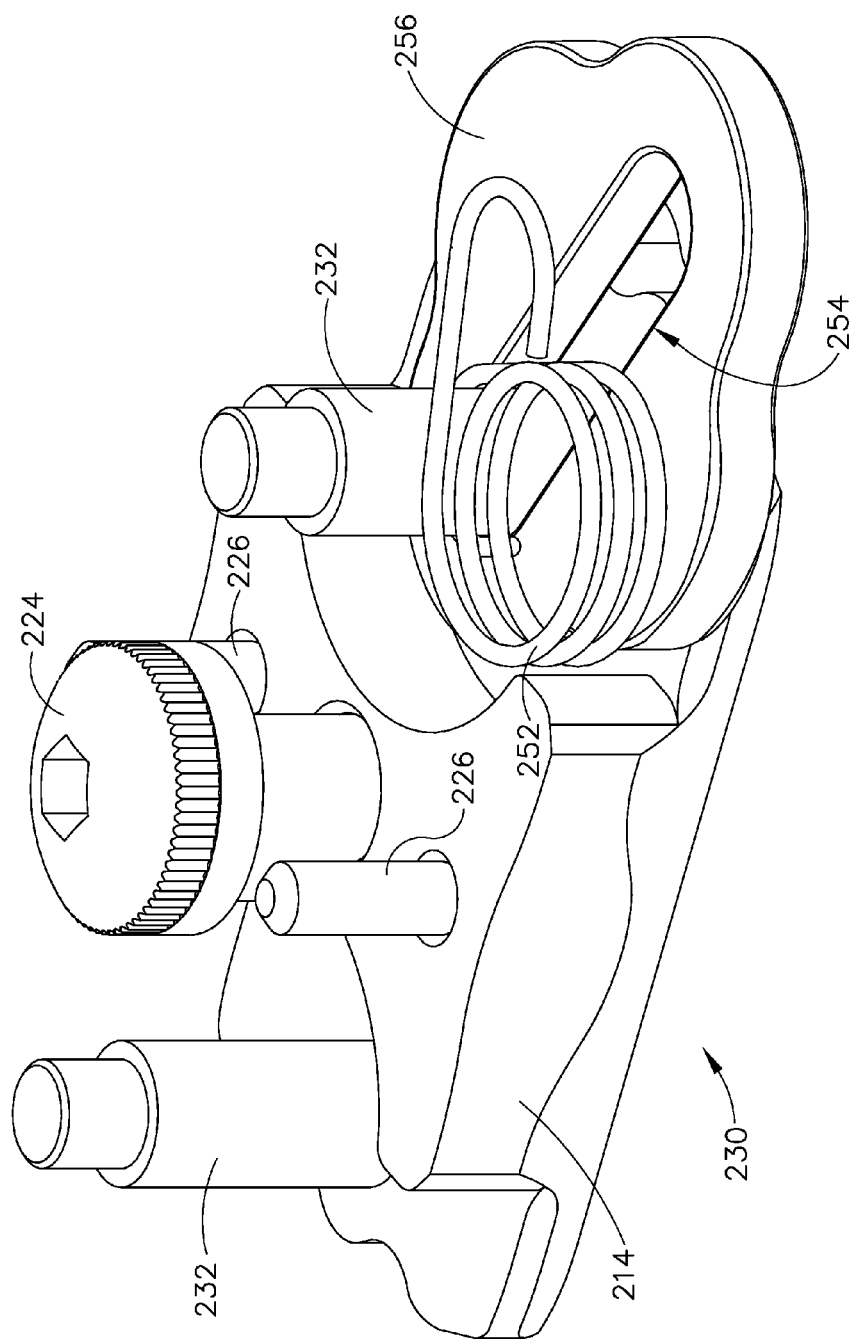
FIG. 44 is an isometric view of a single segment and linking assembly shown with the upper component and link removed.

FIG. 41 depicts an alternative embodiment for the segments and linking assembly of the present invention. In this alternative embodiment, a plurality of segments are again connected together by linking assemblies; however, the segments are modified to increase the strength of the individual segments. Additionally, the segment ends are modified to increase the strength of the positive stop between the components when the segments are flexed to the maximum bending angle, thereby increasing the bending resistance. As shown in FIGS. 41-43, modified segments 212 comprise upper and lower components 220, 230 having an area of increased thickness 214 through the midsection of each component. A hole 216 is bored through the center of upper component 220, and a threaded hole 222 is formed in the center of lower component 230. A screw 224 is inserted into hole 216 and twisted through the threads of hole 222 to secure the upper and lower components 220, 230 together. A pair of vertically extending pins 226 is secured between holes in the upper and lower components 220, 230. Pins 226 are symmetrically positioned on the lateral sides of screw 224. Additionally, a pair of pivot bosses 232 are symmetrically positioned relative to screw 224 along the longitudinal axis of segment 212. Like pins 226, opposite ends of pivot bosses 232 are secured within holes in upper and lower components 220, 230 to fix the bosses perpendicular to the longitudinal segment axis. As shown in FIGS. 43 and 44, pivot bosses 232 are located outside the thickened portion 214 of components 220, 230, to allow space between the upper and lower components for a linking assembly to be mounted on each pivot boss.

In this alternative embodiment, a modified linking assembly 250 comprises a pair of links 256 having a single, oblong opening 254 extending along the longitudinal axis of each link. A tensional spring 252 is located between links 256. Opposite ends of torsional spring 252 are curved to encircle pivot bosses 232, to enable each end of the spring to be mounted on a pivot boss as shown in FIG. 44. Linking assembly 250 is mounted between segments 212, with the first end of torsional spring 252 mounted on a pivot boss in a first segment and the second end of the torsional spring mounted on a pivot boss in a second segment, so that the torsional spring spans between the adjoining segments. The resilient force within spring 252 draws the adjoining segments together, producing a self-straightening effect on the implant member.

As shown in FIG. 41, the ends of segments 212 have a wavy shape, with the direction of the waves alternating between the two ends, so that when joined together the convex surfaces on one segment end are mated with the concave surfaces on the adjacent segment end to nest the segment ends together. Preferably, a series of undulating surfaces are provided on each segment end so that the segment ends nest together in a straight configuration, as well as when the segments are flexed to the maximum bending angle, as shown in FIG. 41. The wavy shaping of the segment ends increases the amount of surface area in contact between the segments as the segments pivot relative to each other. The additional surface contact increases the strength of the positive stop when the corners of the segments make contact at the outer limit of the flex range, in order to prevent overbending. As segments 212 pivot relative to each other, pivot bosses 232 shift within link openings 254. When segments 212 are pivoted to the maximum bending angle, pivot bosses 232 are positioned at opposite ends of link opening 254. The length of link opening 254 thereby controls the maximum bending angle between adjoining segments, as well as the resulting diameter of the curved implant member ends.

Figure 45:
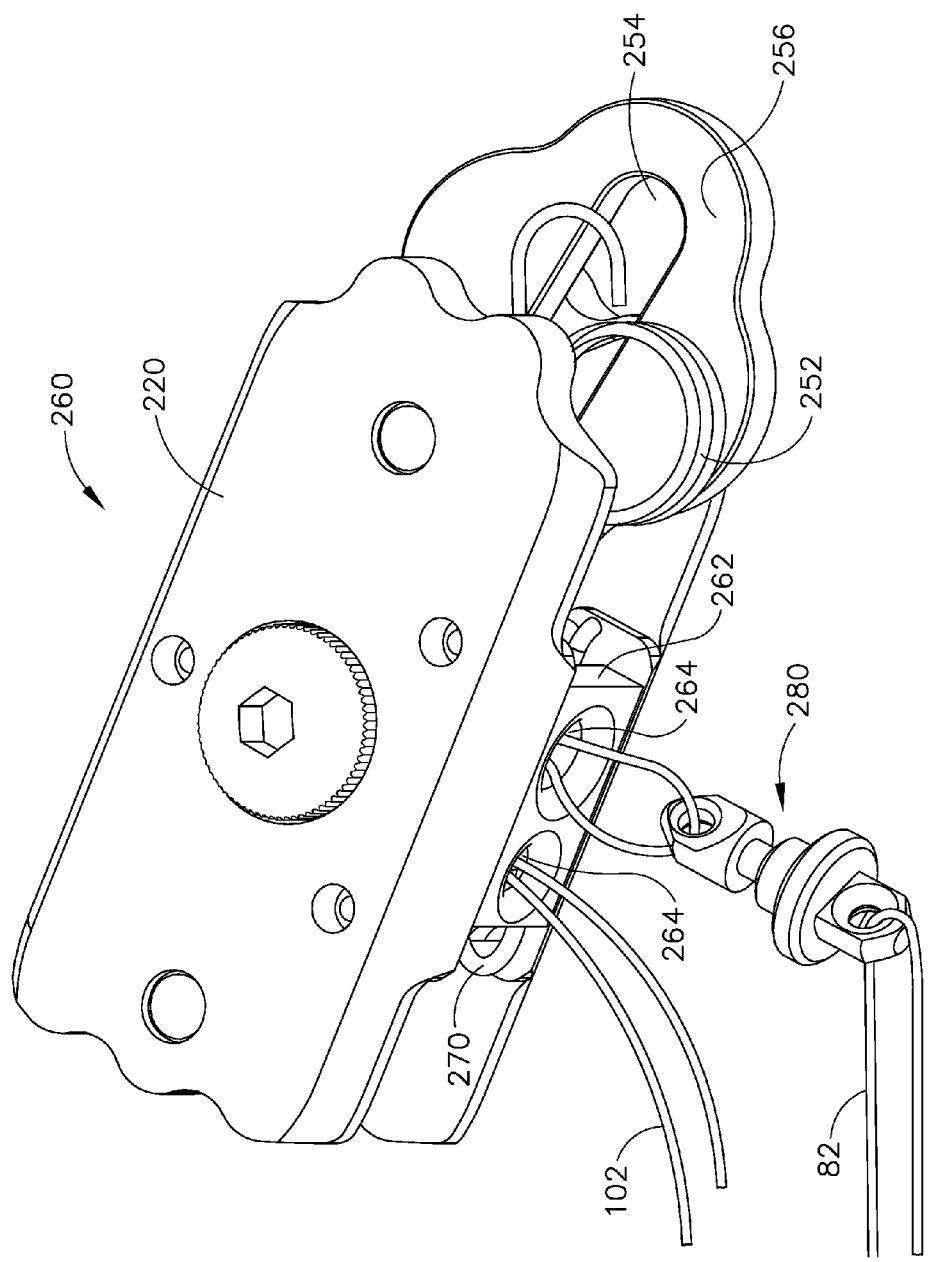
FIG. 45 is an isometric view of a locking segment of the second embodiment of the implant device.
Figure 46:
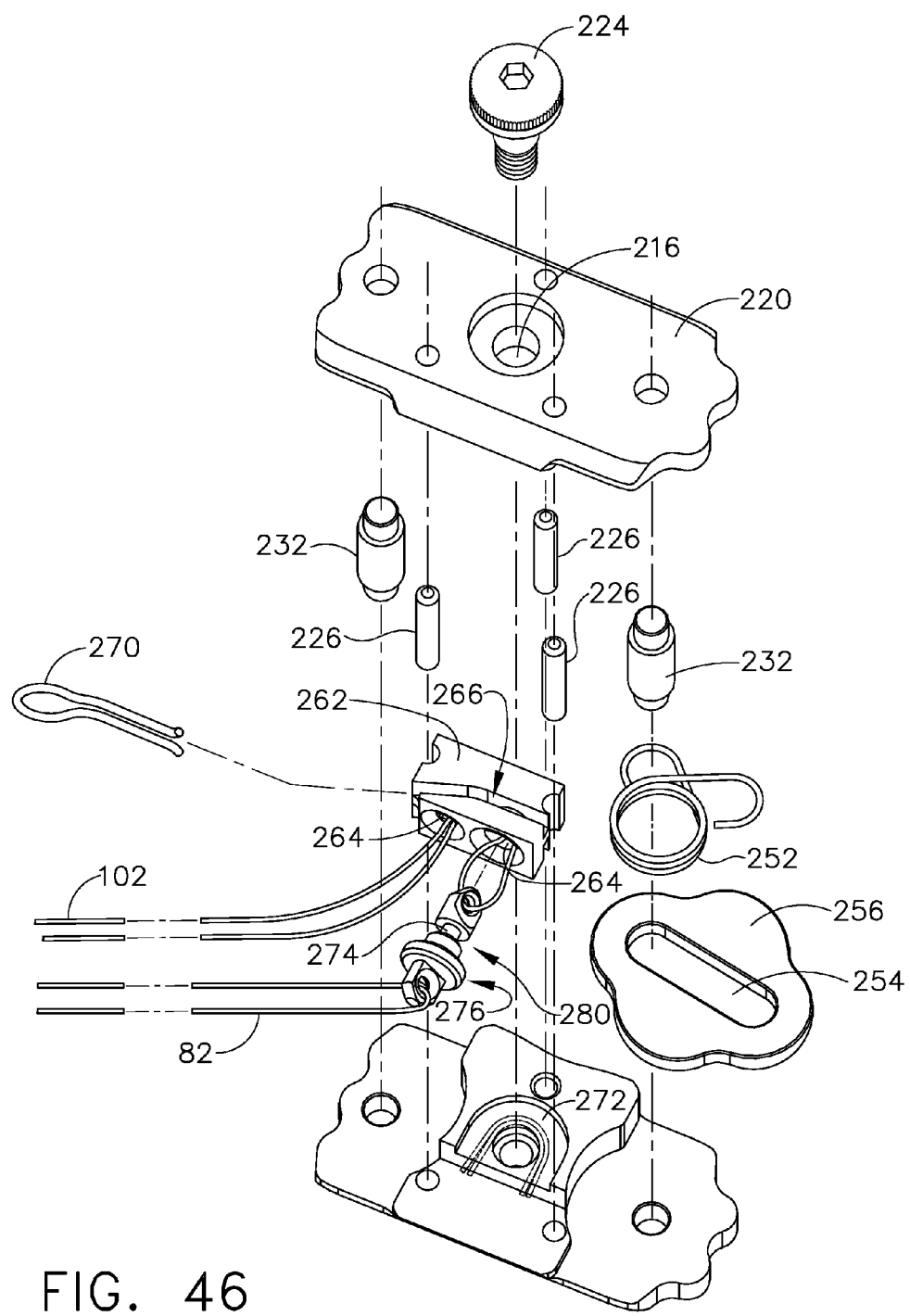
FIG. 46 is an exploded view of the locking segment shown in FIG. 45.

FIG. 45 shows a modified locking segment 260 in accordance with the second embodiment of the invention. As in the previous embodiment, modified locking segment 260 is similar in size and shape to the other segments 212, with the addition of locking elements to secure a tensioning member inside the segment. FIG. 46 is an exploded view of locking segment 260 showing the additional locking elements in greater detail. As shown in these Figures, locking segment 260 includes openings in the inner side of the segment through which a pull cable is routed in and out of the segment. The lower component is modified by removing a portion of the segment midsection 214 and replacing the removed portion with a locking block 262 having a pair of holes 264 drilled through the side of the block. An additional pin 226 is secured between the upper and lower components along the inner side of the segment. The sides of locking block 262 are milled to fit up against pins 226 so that the pins hold the block within the segment. Narrow, longitudinally extending grooves 266 are formed in the upper and lower surfaces of block 262. A spring clip 270 is mounted within grooves 266 with the clip arms extending across block openings 264.

Figure 47:
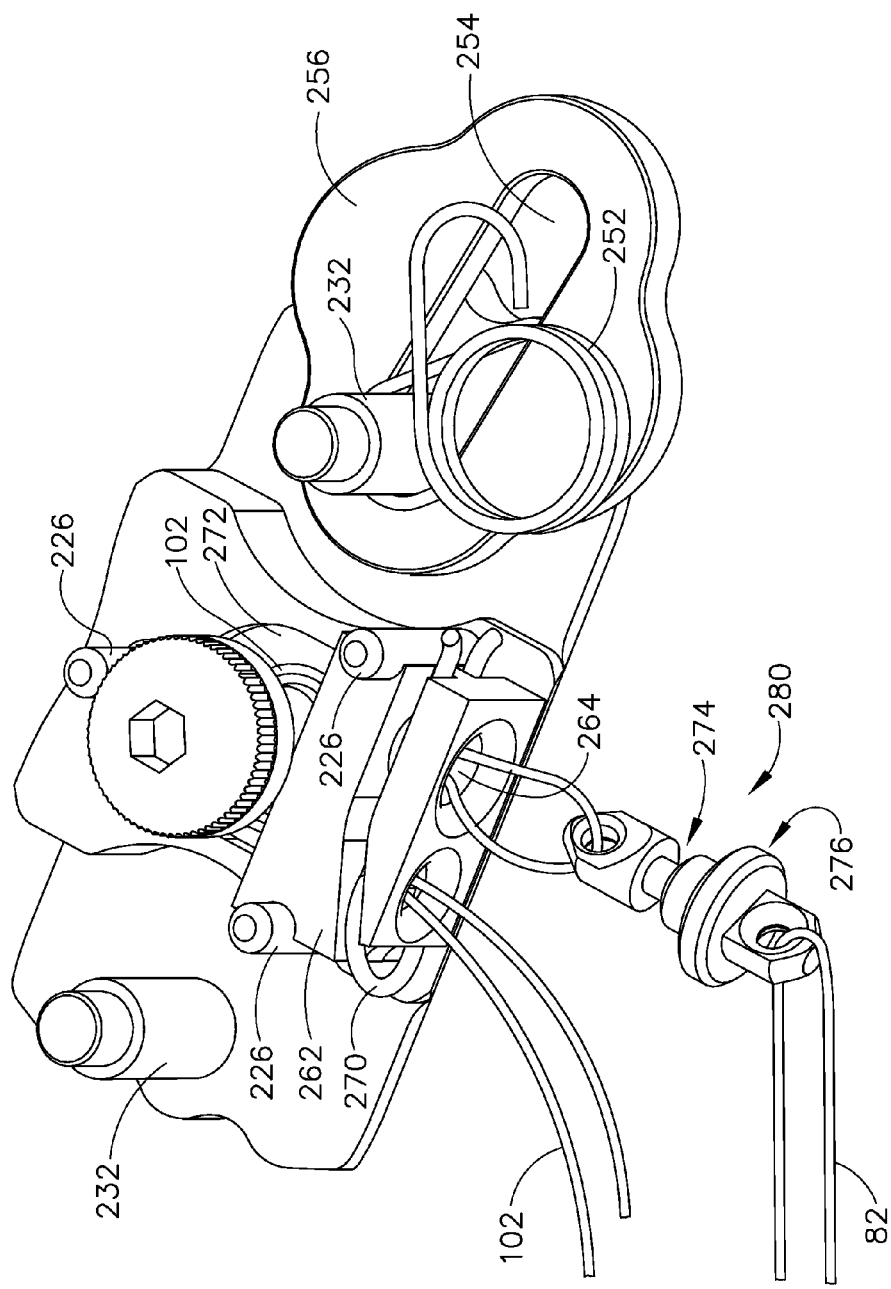
FIG. 47 is an isometric view of the locking segment shown in FIG. 45, showing the segment with the upper component and link removed.

As in the previous embodiment, tensioning members or strings are attached to the distal and proximal most links on the implant member for drawing the end segments into a curved diameter during deployment. In the second embodiment, a modified locking feature 280 is provided on the tensioning strings (proximal string 82 is shown in the Figures). Locking feature 280 includes a hole in a first end through which tensioning string 82 is looped in order to secure the string to the locking feature. The opposite end of locking feature 280 includes a second hole through which the pull cable is looped to attach the pull cable to the locking feature (proximal pull cable 102 is shown in the Figures). Prior to looping through locking feature 280, pull cable 102 is drawn through the interior of locking segment 260. As shown in FIGS. 46-47, pull cable 102 is passed through one of the inner side openings 264, back around the post of screw 224, and then forward through the second inner side opening 264. A channel 272 extends around screw 224, in segment midsection 214, to provide a pathway for pull cable 102. Pull cable 102 is looped through locking feature 280 so that a portion of the cable is passed back through the locking segment in the same fashion. A first end of locking feature 280 has a diameter that is less than the diameter of block opening 264 to enable the first locking feature end to be pulled into the opening during deployment. A band 274 of reduced diameter extends about locking feature 280 adjacent to the first end. Band 274 has sufficient width to allow spring clip 270 to contract into the band as the locking feature is drawn into block 262. A ring 276 of increased diameter extends about locking feature 280 adjacent the second, string connecting end. Ring 276 acts as a plug for locking feature 280, preventing the locking feature from passing fully through the block opening 264.

Figure 48:
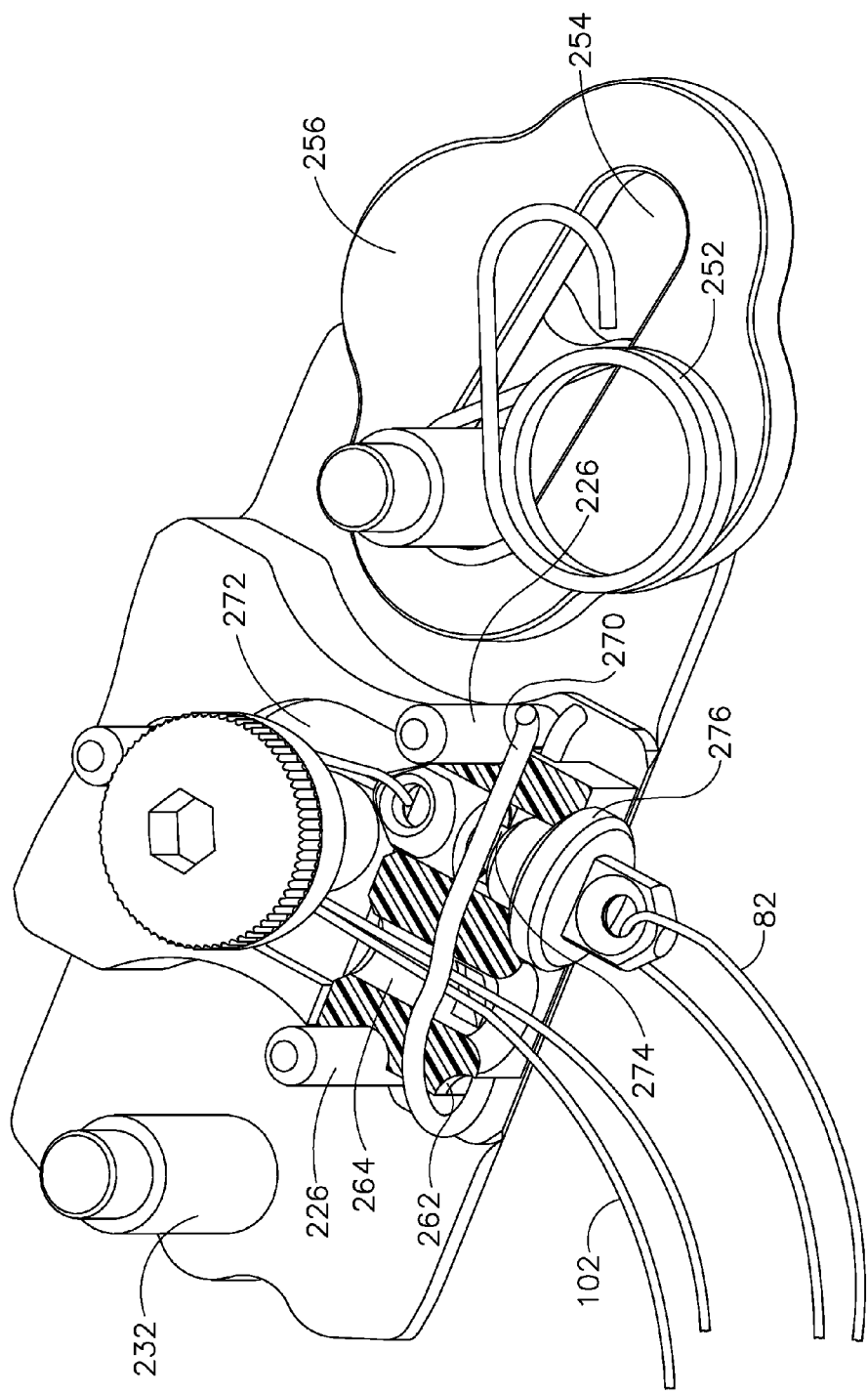
FIG. 48 is an isometric view similar to FIG. 47, showing the locking block in cross-section.

During deployment, tension is applied to pull cable 102 from outside the body. As cable 102 is pulled, the cable moves through channel 272 and openings 264 in locking segment 260. Cable 102 passes out of locking segment 260 and applies force to locking feature 280. The force on locking feature 280 is in turn transferred to tensioning string 82 to draw the end of the implant member in the direction of the locking segment, thereby flexing the segments between the implant member end and the locking segment. As tension continues on pull cable 102, the cable draws locking feature 280 towards and into locking segment opening 264. As locking feature 280 advances into opening 264, spring clip 270 is pushed upward by the tapered first end of the locking feature. As locking feature 280 advances within opening 264, band 274 reaches groove 266, allowing spring clip 270 to contract and lodge inside the band. As clip 270 is engaging band 274, ring 276 is contacting the outside wall of locking block 262, as shown in FIG. 48. The lodging of spring clip 270 inside band 274, and the contact between ring 276 and the side of block 262, prevents further movement of locking feature 280 into the locking segment. Pull cable 102 is prevented from further movement in response to tension on the cable. Likewise, spring clip 270 prevents movement of locking feature 280 in response to a reverse pulling force on string 82. String 82 is held taut by locking feature 280, to maintain the proximal end of the device in a curved shape. Within the curved ends, expanded springs 252 produce an outward force along the length of the curve, which in turn applies pressure against the cavity walls. As mentioned above, FIGS. 45-48 depict a proximal locking segment, as the pull cable is drawn in through the right side of the segment and out the left side, which results in flexing of the segments to the right of the locking segment shown. Although not shown, the distal locking segment would comprise the same locking elements, with the arrangement of the elements reversed to allow the pull cable to enter and exit from the opposite holes in locking block 262.

As the pull cable is being tensioned and drawn through locking segment 260, segments 212 in the proximal section of the implant member are pivoting relative to linking assemblies 250. As the segments pivot, the segments shift or roll along the adjoining ends from contact between the concave center of the distal segment and convex center of the proximal segment, to contact between the concave corner of the distal segment and the convex corner of the proximal segment, as shown in FIG. 41. End segments 12 flex into the minimum curve diameter (i.e. maximum bending angle), with the corner edges touching as shown, as spring clip 270 is latching onto locking feature 280 inside the locking segment. When segments 12 are flexed to the maximum bending angle, the extra surface contact along the segment corners reduces the likelihood of one segment riding over the top of the other segment (and thereby reducing the curved end diameter) during periods of increased pressure on the implant device.

The exemplary device embodiments described herein are retrievable in the event of unforeseen complications, or after a predefined period of time either to end the intervention, to make adjustments to the device, or to replace the device with one having different characteristics (size, shape, stiffness, features, etc.). The device may be retrieved endoscopically by manipulating the device to return the device to a relatively straight configuration. Tensioning members 80, 82, or other means utilized to hold the device in the operative configuration, are released to allow endoscopic removal of the device. Alternative methods may also be used to retrieve the device, with the device design allowing the device to be retrieved in a minimally invasive manner that is atraumatic to the patient.

The implant device described herein effectively flattens the gastric cavity, reducing the effective volume per surface area of stomach tissue. The pressure of the device against the cavity wall increases the wall tension and biases stretch receptors to send an early sense of satiety. The stretching of the stomach tissue inhibits gastric motility and delays gastric emptying. The device can be implanted so as to partially block the pyloric outlet, delaying gastric emptying. Alternatively, the device could be implanted to provide a restrictive element just distal of the esophageal gastric junction.

The foregoing description of preferred embodiments of the invention has been presented for purposes of illustration and description. It is not intended to be exhaustive or to limit the invention to the precise form disclosed. Obvious modifications or variations are possible in light of the above teachings.

The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. An implant for placement within a hollow body organ, said implant comprising:
   a. a member having distal and proximal ends, said member has an undeployed shape for delivery to the hollow body and a deployed shape for implantation therein said member comprising a plurality of individual segments connected together wherein said segments can be flexed relative to each other, said plurality of segments defining a common plane in the undeployed shape;
   b. at least one tensioning tether having a first end attached to at least one of said distal and proximal end and a second end attached to said member between said distal and proximal ends, wherein applying tension to said tether moves said member towards said deployed shape, said deployed shape comprising a curved shape in the common plane.

2. The implant of claim 1 wherein said member comprises a plurality of segments movably connected to each other in said undeployed shape, and a means for attaching said segments to each other when placing said member in said deployed shape.

3. The implant of claim 1 wherein said member has an exterior surface for contacting said hollow body and wherein said exterior surface has a plurality of peaks and valleys disposed thereon.

4. The implant of claim 1 wherein said member has an exterior surface for contacting said hollow body and wherein said member has an elastomer coating.

5. The implant of claim 1 wherein said member comprises a plurality of segments movably connected to each other in said undeployed shape, and a means for attaching said segments to each other when placing said member in said deployed shape.

6. The implant of claim 1 wherein said member has an exterior surface for contacting said hollow body and wherein said exterior surface has a plurality of peaks and valleys disposed thereon.

7. The implant of claim 1 wherein said member has an exterior surface for contacting said hollow body and wherein said member has an elastomer coating.

8. An implant for placement within a hollow body organ, said implant comprising:
   a. a member having distal and proximal ends, said member has substantially linear shape for delivery to the hollow body and a substantially rigid curved shape for implantation therein said member comprising a plurality of individual segments connected together wherein said segments can be flexed relative to each other, said plurality of individual segments defining a common plane when in a linear shape for delivery;
   b. a deployment mechanism for bending said member so as to place it in said curved shape in the common plane, said member having a first rate at which it initially resists bending, and a second substantially higher rate at which it resists further bending.

* * * * *